(12) United States Patent
Cornet et al.

(10) Patent No.: US 9,474,883 B2
(45) Date of Patent: Oct. 25, 2016

(54) ADAPTABLE WOUND DRAINAGE SYSTEM

(71) Applicant: KCI Licensing, Inc., San Antonio, TX (US)

(72) Inventors: Douglas A. Cornet, San Antonio, TX (US); Michael Manwaring, San Antonio, TX (US); Edward Sy Griffey, Fair Oaks Ranch, TX (US); Erin Black, Middlesex, NJ (US); Colin John Hall, Poole (GB); Jonathan Kagan, Hopkins, MN (US)

(73) Assignee: IC Surgical, Inc., Grand Rapids, MI (US)

( * ) Notice: Subject to any disclaimer, the term of this patent is extended or adjusted under 35 U.S.C. 154(b) by 144 days.

(21) Appl. No.: 14/082,906

(22) Filed: Nov. 18, 2013

(65) Prior Publication Data

US 2014/0163532 A1    Jun. 12, 2014

Related U.S. Application Data

(60) Provisional application No. 61/734,295, filed on Dec. 6, 2012.

(51) Int. Cl.
*A61M 27/00* (2006.01)
*A61M 1/00* (2006.01)
(Continued)

(52) U.S. Cl.
CPC ........... *A61M 27/00* (2013.01); *A61M 1/0039* (2013.01); *A61M 1/0088* (2013.01);
(Continued)

(58) Field of Classification Search
CPC ........... A61M 1/0088; A61M 1/0039; A61M 27/00; A61M 2025/0034; A61M 25/0668; A61M 25/0662; A61M 2025/0675; A61M 2025/006; A61M 25/0032; A61M 2025/004; A61M 2025/0059; A61M 2025/0063; A61M 25/0029; A61M 25/0071; A61M 25/0102; A61M 2025/09133; A61M 2025/0915; G02B 6/44; G02B 6/4495
See application file for complete search history.

(56) References Cited

U.S. PATENT DOCUMENTS 764,779 A * 7/1904 Stone .................. F16L 9/18
                                                    138/115
1,355,846 A   10/1920 Rannells
(Continued)

FOREIGN PATENT DOCUMENTS

AU    550575 A1    3/1986
AU    745271       4/1999
(Continued)

OTHER PUBLICATIONS

International Search Report for Corresponding PCT, Apr. 25, 2014.
(Continued)

*Primary Examiner* — Adam Marcetich
(74) *Attorney, Agent, or Firm* — Thomas Engellenner; Reza Mollaaghababa; Pepper Hamilton, LLP

(57) ABSTRACT

Provided are drainage systems that may include a drainage manifold and may be suitable for draining fluid from a tissue site. The drainage manifold may include a plurality of elongate members having a moveable end that may be adapted to configure the drainage manifold to treat a uniquely shaped tissue site. The drainage manifold may be coupled to a drainage tube with a transitional connector to provide a drainage system capable of distributing reduced pressure to the tissue site to enhance the drainage of fluids.

26 Claims, 12 Drawing Sheets

(51) Int. Cl.
*A61M 25/00* (2006.01)
*A61M 25/06* (2006.01)
*G02B 6/44* (2006.01)

(52) U.S. Cl.
CPC ..... *A61M 25/0032* (2013.01); *A61M 25/0071* (2013.01); *A61M 25/0668* (2013.01); *A61M 2025/004* (2013.01); *A61M 2025/0034* (2013.01); *A61M 2025/0063* (2013.01); *A61M 2025/0675* (2013.01); *G02B 6/4495* (2013.01)

(56) References Cited

U.S. PATENT DOCUMENTS

| | | |
|---|---|---|
| 2,547,758 A | 4/1951 | Keeling |
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,402,685 A * | 9/1983 | Buhler ............... A61L 29/049 525/931 |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,692,153 A * | 9/1987 | Berlin ............... A61M 27/00 604/171 |
| 4,710,165 A | 12/1987 | McNeil et al. |
| 4,717,379 A * | 1/1988 | Ekholmer ........... A61M 25/007 604/43 |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,867,747 A * | 9/1989 | Yarger ............... A61M 1/008 604/263 |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,925,452 A * | 5/1990 | Melinyshyn .......... A61M 25/00 138/111 |
| 4,941,882 A | 7/1990 | Ward et al. |
| 4,950,232 A * | 8/1990 | Ruzicka ............... A61M 1/008 604/103.01 |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,395 A * | 3/1992 | Rosenberg .......... A61M 1/0005 604/247 |
| 5,100,396 A | 3/1992 | Zamierowski |
| 5,116,310 A | 5/1992 | Seder |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 5,800,414 A * | 9/1998 | Cazal ................. A61M 25/00 604/264 |
| 5,891,111 A * | 4/1999 | Ismael ............... A61M 25/0021 138/116 |
| 5,947,953 A * | 9/1999 | Ash .................. A61M 25/0021 138/115 |
| 6,071,267 A | 6/2000 | Zamierowski |
| 6,099,513 A | 8/2000 | Spehalski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,491,693 B1 | 12/2002 | Lytinas |
| 6,493,568 B1 | 12/2002 | Bell et al. |
| 6,540,734 B1 * | 4/2003 | Chiu ................. A61M 25/1011 604/508 |
| 6,553,998 B2 | 4/2003 | Heaton et al. |
| 6,814,079 B2 | 11/2004 | Heaton et al. |
| 6,840,960 B2 | 1/2005 | Bubb |
| 7,658,735 B2 | 2/2010 | Spehalski |
| 7,790,945 B1 | 9/2010 | Watson, Jr. |
| 7,824,384 B2 | 11/2010 | Watson, Jr. |
| 8,109,932 B2 | 2/2012 | Lytinas |
| 8,221,393 B1 * | 7/2012 | Placik ............... A61M 25/0009 604/35 |
| 8,235,939 B2 | 8/2012 | Johnson et al. |
| 8,246,948 B2 | 8/2012 | Swain |
| 8,267,918 B2 | 9/2012 | Johnson et al. |
| 8,435,213 B2 | 5/2013 | Cornet et al. |
| 8,603,074 B2 | 12/2013 | Kagan |
| 8,617,140 B2 | 12/2013 | Johnson et al. |
| 8,702,711 B2 | 4/2014 | Griffey et al. |
| 8,715,267 B2 | 5/2014 | Bengtson et al. |
| 8,795,245 B2 | 8/2014 | Collins |
| 8,864,728 B2 | 10/2014 | Long et al. |
| 8,894,620 B2 | 11/2014 | Swain |

(56) References Cited

U.S. PATENT DOCUMENTS

| | | | |
|---|---|---|---|
| 8,939,933 | B2 | 1/2015 | Santora et al. |
| 9,050,402 | B2 | 6/2015 | Johnson et al. |
| 2002/0077661 | A1 | 6/2002 | Saadat |
| 2002/0115951 | A1 | 8/2002 | Norstrem et al. |
| 2002/0120185 | A1 | 8/2002 | Johnson |
| 2002/0143286 | A1 | 10/2002 | Tumey |
| 2003/0004493 | A1* | 1/2003 | Casey ............... A61M 25/005 604/525 |
| 2003/0135148 | A1* | 7/2003 | Dextradeur ....... A61M 25/0662 604/8 |
| 2003/0225347 | A1 | 12/2003 | Argenta et al. |
| 2004/0006331 | A1 | 1/2004 | Shchervinsky |
| 2004/0039391 | A1 | 2/2004 | Argenta et al. |
| 2006/0079852 | A1 | 4/2006 | Bubb et al. |
| 2006/0133746 | A1* | 6/2006 | Quinn ................. G02B 6/4495 385/100 |
| 2010/0069829 | A1 | 3/2010 | Hutchinson |
| 2010/0168688 | A1* | 7/2010 | Santora ................. A61B 17/88 604/313 |
| 2010/0179493 | A1* | 7/2010 | Heagle ................ A61M 1/0001 604/313 |
| 2010/0305509 | A1* | 12/2010 | Osypka ............. A61M 25/0668 604/164.05 |
| 2011/0054283 | A1 | 3/2011 | Shuler |
| 2011/0220388 | A1* | 9/2011 | Sabaris ................. H01B 7/184 174/113 R |
| 2011/0276022 | A1* | 11/2011 | O'Day .............. A61M 25/0021 604/500 |
| 2012/0116469 | A1 | 5/2012 | Lytinas |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| JP | 4129536 | 4/1992 |
| SG | 71559 | 4/2002 |
| WO | 80/02182 | 10/1980 |
| WO | 87/04626 | 8/1987 |
| WO | 90/10424 | 9/1990 |
| WO | 93/09727 | 5/1993 |
| WO | 94/20041 | 9/1994 |
| WO | 96/05873 | 2/1996 |
| WO | 97/18007 | 5/1997 |
| WO | 99/13793 | 3/1999 |

OTHER PUBLICATIONS

N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (certified translation).

Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), vol. 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.

Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, p. 1.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., vol. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

(56) References Cited

OTHER PUBLICATIONS

G. Živadinovic, V. Đukić, Ž. Maksimović, Đ. Radak, and P. Peška, "Vacuum Therapy in the Treatment of Peripheral Blood Vessels," Timok Medical Journal 11 (1986), pp. 161-164 (certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, "An Improved Sump Drain-Irrigation Device of Simple Construction," Archives of Surgery 105 (1972) pp. 511-513.

C.E. Tennant, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, the Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians (Jul. 2007).

\* cited by examiner

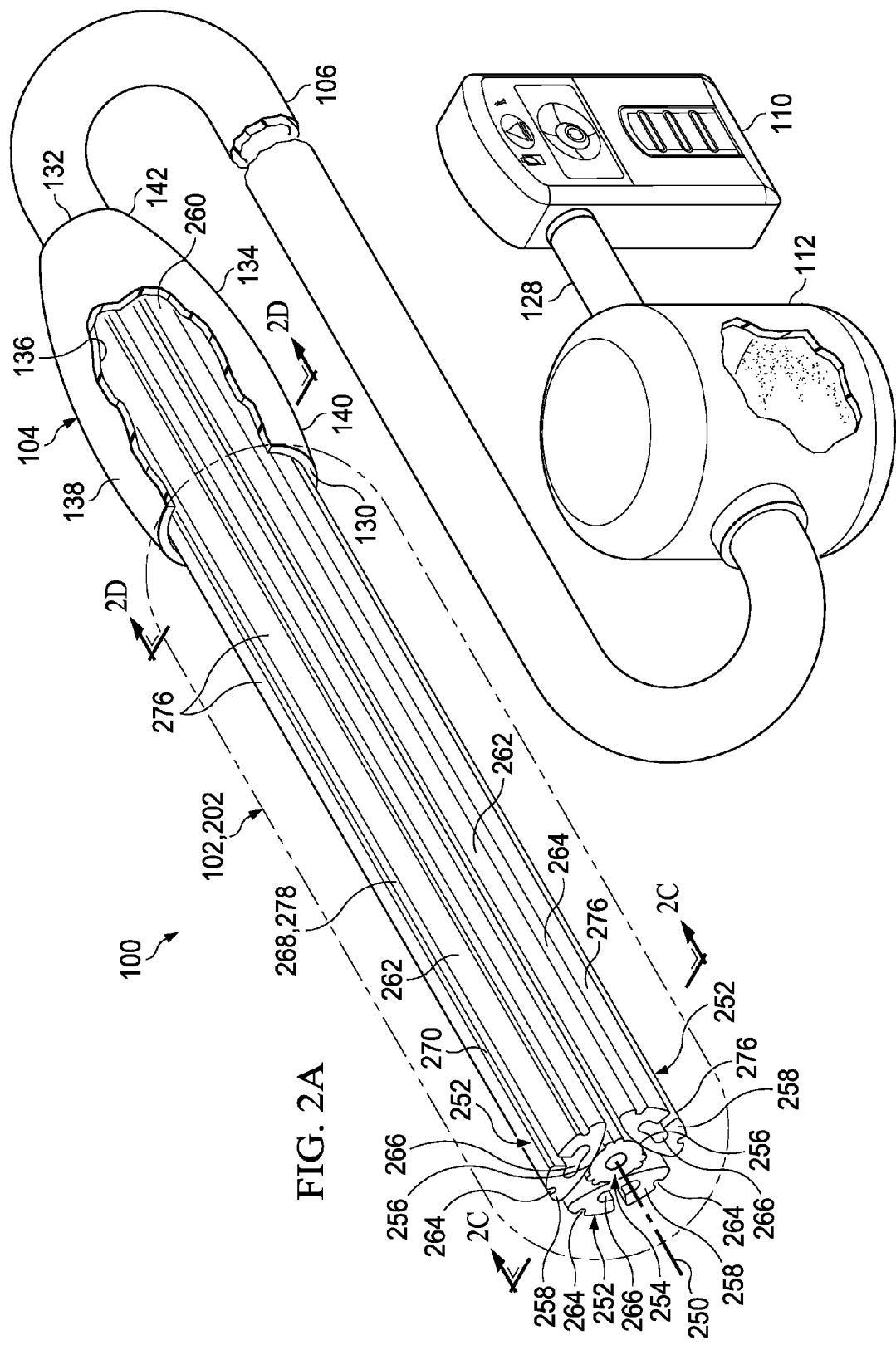

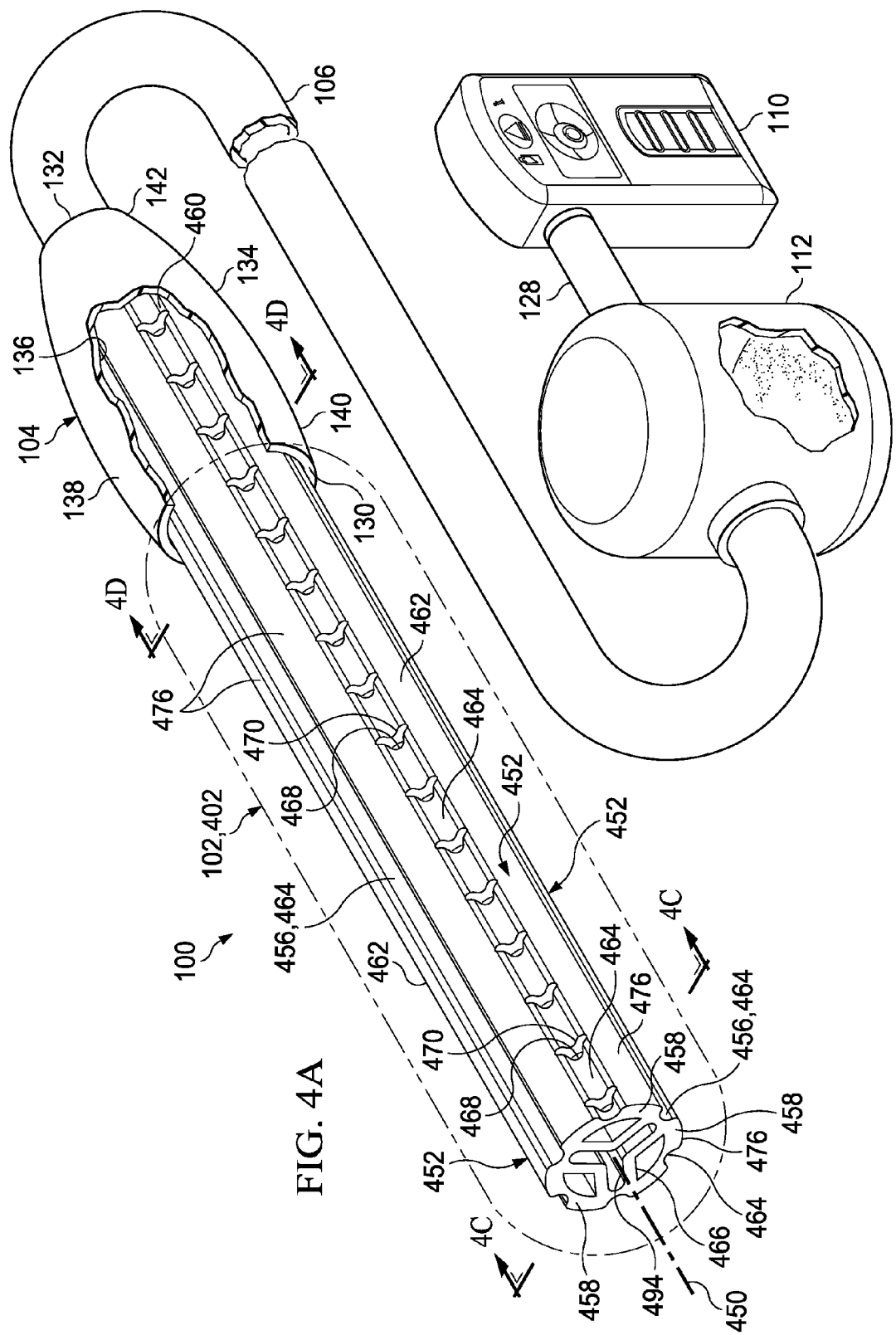

ADAPTABLE WOUND DRAINAGE SYSTEM

RELATED APPLICATION

This application claims the benefit, under 35 USC §119 (e), of the filing of U.S. Provisional Patent Application Ser. No. 61/734,295, entitled "Adaptable Wound Drainage System," filed Dec. 6, 2012, which is incorporated herein by reference for all purposes.

BACKGROUND

The subject matter disclosed herein relates generally to medical wound care systems, and more particularly, but not by way of limitation, to wound drainage devices, systems, and methods. The devices, systems, and methods disclosed may provide increased configurability for adapting to multi-dimensional wounds, and may be particularly suitable for use with reduced pressure to enhance the drainage of fluids from the wound.

Common wound drainage devices, systems, and methods typically require multiple incision sites in a patient to provide treatment for a multi-dimensional wound that may have a large surface area or an unusual shape. Further, known devices, systems, and methods are typically difficult to configure and seal at the wound site, and can cause damage to tissue and pain for the patient upon removal.

Thus, improvements to wound drainage devices, systems, and methods that provide increased configurability and ease of placement for treatment of multi-dimensional wounds while reducing the potential for damage to tissue and pain for the patient are desirable. Such improvements may reduce the chance of infection, improve cosmetic appearance, reduce the pooling of fluids, and reduce the potential for seroma or hematoma.

SUMMARY

Shortcomings with certain aspects of wound drainage devices, systems, and methods are addressed as shown and described in a variety of illustrative, non-limiting embodiments herein.

According to an illustrative, non-limiting embodiment, a drainage system for draining fluid from a tissue site may include a drainage manifold, a transitional connector, and a drainage tube. The drainage manifold may have a longitudinal axis and may include a plurality of elongate members each having a first end, a second end, and an outer wall. The first end of each of the elongate members may be moveable between a gathered position and a dispersed position relative to the longitudinal axis of the drainage manifold. When the first end of each of the elongate members is in the gathered position, the elongate members may be releaseably secured longitudinally and circumferentially about the longitudinal axis of the drainage manifold. Each of the elongate members may further include a longitudinal duct and a reinforced portion. The longitudinal duct may be positioned on the outer wall and between the first end and the second end of the elongate members. The reinforced portion may be positioned between the first end and the second end of the elongate members. The transitional connector may have a first end and an opposing second end. The first end of the transitional connector may be coupled to the drainage manifold. The drainage tube may be coupled to the second end of the transitional connector and in fluid communication with the drainage manifold and the longitudinal duct of each of the elongate members.

According to another illustrative, non-limiting embodiment, a drainage system for draining fluid from a tissue site may include a drainage manifold, a transitional connector, and a drainage tube. The drainage manifold may have a longitudinal axis and may include an elongate support, a plurality of elongate members, and a plurality of sacrificial webs. The elongate support may have a length and an external surface. The length of the elongate support may be positioned on the longitudinal axis of the drainage manifold. The plurality of elongate members may each have a first end, a second end, and an outer wall. The first end of each of the elongate members may be moveable between a gathered position and a dispersed position relative to the longitudinal axis of the drainage manifold. When the first end of the elongate member is in the gathered position, the elongate member may be releaseably secured longitudinally and circumferentially about the external surface of the elongate support. Each of the elongate members may further include a longitudinal duct positioned on the outer wall and between the first end and the second end of the elongate member. At least one of the plurality of sacrificial webs may be positioned between the elongate member and the elongate support to releaseably secure the elongate member about the elongate support when the first end of the elongate member is in the gathered position. The transitional connector may have a first end and an opposing second end. The first end of the transitional connector may be coupled to the drainage manifold. The drainage tube may be coupled to the second end of the transitional connector and in fluid communication with the drainage manifold and the longitudinal duct of each of the elongate members.

According to yet another illustrative, non-limiting embodiment, a drainage manifold for draining fluid from a tissue site may have a longitudinal axis and may include an elongate support, a plurality of elongate members, and a plurality of sacrificial webs. The elongate support may have a length, an external surface, and an inner lumen. The length of the elongate support may be positioned on the longitudinal axis of the drainage manifold. The plurality of elongate members may each have a first end, a second end, and an outer wall. The first end of each of the elongate members may be moveable between a gathered position and a dispersed position relative to the longitudinal axis of the drainage manifold. When the first end of the elongate member is in the gathered position, the elongate member may be releaseably secured longitudinally and circumferentially about the external surface of the elongate support. Each of the elongate members may further include a longitudinal duct positioned on the outer wall and between the first end and the second end of the elongate member, an inner lumen, and an opening disposed through the outer wall. The opening may provide fluid communication between the inner lumen of the elongate member and the outer wall. At least one of the plurality of sacrificial webs may be positioned between the elongate member and the elongate support to releaseably secure the elongate member about the elongate support when the first end of the elongate member is in the gathered position.

According to still another illustrative, non-limiting embodiment, a drainage system for draining fluid from a tissue site may include a drainage manifold, a reduced-pressure source, and a fluid canister. The drainage manifold may include an elongate support and a plurality of elongate members. The elongate support may have a length, an external surface, an inner lumen, and a plurality of openings disposed through the external surface to provide fluid communication between the external surface and the inner lumen. The plurality of elongate members may each have a first end, a second end, and an outer wall. The first end of each of the elongate members may be moveable relative to the elongate support. The second end of each of the elongate members may be secured about the external surface of the elongate support. The outer wall of each of the elongate members may be in fluid communication with the inner lumen in the elongate support. The reduced-pressure source may be fluidly coupled to the elongate support and adapted to provide a reduced pressure to the drainage manifold and the inner lumen in the elongate support. The fluid canister may be positioned in fluid communication between the elongate support and the reduced-pressure source. The fluid canister may be adapted to retain fluid communicated from the drainage manifold.

Other features and advantages of the illustrative embodiments will become apparent with reference to the drawings and detailed description that follow.

BRIEF DESCRIPTION OF THE DRAWINGS

A more complete understanding of this specification may be obtained by reference to the following detailed description when taken in conjunction with the accompanying drawings, wherein:

FIG. 2A is a perspective, cut-away view of an illustrative embodiment of a drainage system depicting a drainage manifold having a plurality of elongate members in a gathered position;

FIG. 4A is a perspective, cut-away view of another illustrative embodiment of a drainage system depicting a drainage manifold having a plurality of elongate members in a gathered position;

DETAILED DESCRIPTION

Figure 1:
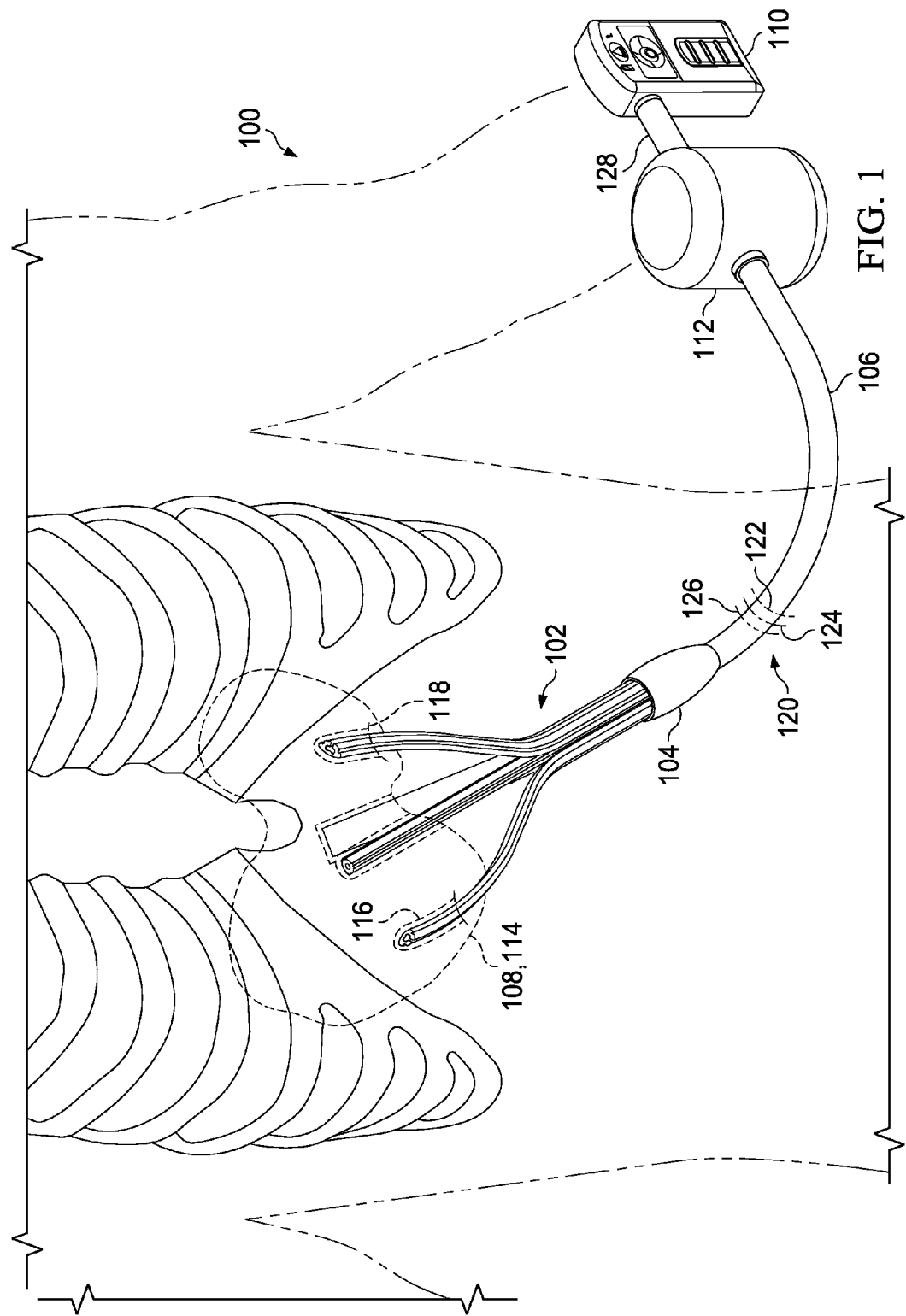
FIG. 1 is a perspective view of an illustrative embodiment of a drainage system applied to a tissue site.

In the following detailed description of the non-limiting, illustrative embodiments, reference is made to the accompanying drawings that form a part hereof. Other embodiments may be utilized and logical, structural, mechanical, electrical, and chemical changes may be made without departing from the scope of this specification. To avoid detail not necessary to enable those skilled in the art to practice the embodiments described herein, the detailed description may omit certain information known to those skilled in the art. The following detailed description is, therefore, provided without limitation and with the scope of the illustrative embodiments being defined by the appended claims. As used herein, unless otherwise indicated, "or" does not require mutual exclusivity.

Referring generally to drawing FIGS. 1-5B, depicted therein are illustrative embodiments of a drainage system 100 that may include a drainage manifold 102, a transitional connector 104, and a drainage tube 106. The drainage system 100 may be particularly suitable for treating a tissue site 108, and may utilize reduced pressure to enhance the drainage of fluids from the tissue site 108. Thus, the drainage system 100 may additionally include a reduced-pressure source 110 adapted to provide reduced pressure as part of the drainage system 100. Further, the drainage system 100 may include a fluid canister 112 adapted to retain fluid extracted from, for example, the tissue site 108.

The tissue site 108 may be, for example, a multi-dimensional tissue site 114 that may include multiple cavities 116 requiring drainage or treatment. The cavities 116 may be positioned or otherwise formed between multiple tissue layers 118. As depicted in FIG. 1, for example, the drainage system 100 may be applied to the tissue site 108 through an incision 120 that extends through or otherwise involves epidermis 122, dermis 124, and subcutaneous tissue 126. The drainage system 100 may be utilized at other tissue sites.

The tissue site 108 may be the bodily tissue of any human, animal, or other organism, including bone tissue, adipose tissue, muscle tissue, dermal tissue, vascular tissue, connective tissue, cartilage, tendons, ligaments, or any other tissue. Treatment of the tissue site 108 may include the removal of fluids, such as, for example, exudate or ascites, or the instillation of fluid to the tissue site 108.

As used herein, "reduced pressure" generally refers to a pressure less than the ambient pressure at the tissue site 108 being subjected to treatment. This reduced pressure may be less than the atmospheric pressure. In some embodiments, the reduced pressure may be less than a hydrostatic pressure at a tissue site. Unless otherwise indicated, values of pressure stated herein are gauge pressures. While the amount and nature of reduced pressure applied to a tissue site may vary according to the application, the reduced pressure may be between about −5 mm Hg to about −500 mm Hg. In some embodiments, the reduced pressure may be in a therapeutic range between about −100 mm Hg to about −200 mm Hg.

The reduced pressure delivered may be constant or varied, patterned or random, and may be delivered continuously or intermittently. Although the terms "vacuum" and "negative pressure" may be used to describe the pressure applied to a tissue site, the actual pressure applied to a tissue site may be more than the pressure normally associated with a complete vacuum. Consistent with the use herein, an increase in reduced pressure or vacuum pressure typically refers to a relative reduction in absolute pressure.

In the embodiments of FIGS. 1-5B, the reduced-pressure source 110 may be fluidly coupled to the drainage tube 106. The drainage tube 106 may be in fluid communication with the transitional connector 104 and the drainage manifold 102 as will be described below. Further, the fluid canister 112 may be fluidly coupled between the drainage tube 106 and the reduced-pressure source 110. As shown, the drainage tube 106 may be fluidly coupled to the fluid canister 112. A fluid conduit 128 may be coupled between the fluid canister 112 and the reduced-pressure source 110 to provide fluid communication and reduced pressure from the reduced-pressure source 110 to, for example, the fluid canister 112, the drainage tube 106, the transitional connector 104, and the drainage manifold 102. The drainage tube 106 and the fluid conduit 128 may be coupled to an upper portion of the fluid canister 112 to prevent the reduced pressure from interfering with fluid collecting at a lower portion of the fluid canister 112.

As used herein, the term "coupled" may include coupling with a separate object or direct coupling. The term "coupled" may also encompass two or more components that are continuous with one another by virtue of each of the components being formed from the same piece of material. Also, the term "coupled" may include chemical coupling, such as with a chemical bond, or mechanical, thermal, or electrical coupling. Fluid coupling may refer to a coupling permitting fluid to be in communication between the designated parts or locations.

The reduced-pressure source 110 may be any suitable device for providing reduced pressure as described herein, such as, for example, a vacuum pump, wall suction, or other source. The fluid canister 112 may be any suitable containment device capable of retaining fluid and communicating reduced pressure from the reduced-pressure source 110 to other components of the drainage system 100, such as the drainage manifold 102.

In some embodiments, one or more monitoring devices (not shown) may be fluidly coupled to the drainage system 100. The monitoring devices may be, for example, a pressure-feedback device, a volume detection system, a blood detection system, an infection detection system, a flow monitoring system, a temperature monitoring system, or similar device. In some embodiments, the monitoring devices may be formed integrally with the reduced-pressure source 110.

The transitional connector 104 may have a first end 130, an opposing second end 132, a center 134 positioned substantially equidistant between the first end 130 and the second end 132, an internal surface 136, and an external surface 138. The first end 130 of the transitional connector 104 may be fluidly coupled to the drainage manifold 102, and the second end 132 of the transitional connector 104 may be fluidly coupled to the drainage tube 106. Thus, the drainage tube 106 may be in fluid communication with the drainage manifold 102. The transitional connector 104 may be adapted to provide a smooth external profile between the drainage manifold 102 and the drainage tube 106. For example, in some embodiments, the transitional connector 104 may have a first taper 140 and an opposing second taper 142. The first taper 140 may provide a tapered transition from an outside diameter at the center 134 of the transitional connector 104 to a smaller outside diameter at the first end 130 of the transitional connector 104. Similarly, the second taper 142 may provide a tapered transition from the outside diameter at the center 134 to a smaller outside diameter at the second end 132 of the transitional connector 104. The first taper 140 and the second taper 142 may have any shape or angle to provide an external profile for the transitional connector 104 suitable for a particular application. In other embodiments, the transitional connector 104 may be omitted and the drainage manifold 102 may be coupled to the drainage tube 106 or formed integrally with the drainage tube 106. Further, in some embodiments, the external surface 138 and the internal surface 136 of the transitional connector 104 may have a substantially circular cross-section.

The drainage manifold 102, the transitional connector 104, and the drainage tube 106 may be formed, for example, from a soft polymer or other pliable material. As non-limiting examples, the drainage manifold 102, the transitional connector 104, and the drainage tube 106 may be formed from a silicone elastomer, polyurethane, polyethylene, polypropylene, polyvinyl chloride (PVC), fluorosilicone, ethylene-propylene, acrylic, or similar material. In some embodiments, the drainage manifold 102 may be extruded from DEHP-free PVC. In another embodiment, the drainage manifold 102, the transitional connector 104, and the drainage tube 106 may be molded, casted, or extruded, and may be formed as an integral unit. In yet another embodiment, the transitional connector 104 may be a silicone curable adhesive bonded joint for coupling the drainage manifold 102 and the drainage tube 106 to one another. To suit a particular application, the drainage manifold 102 may additionally include color-coding, materials for X-Ray detection, graduation markings, and coatings to reduce clogging and the presence of bacteria.

Referring now to the embodiments of FIGS. 2A-2D, a drainage manifold 202 may have a longitudinal axis 250 and may include a plurality of elongate members 252, an elongate support 254, and a plurality of sacrificial webs 256. Each of the elongate members 252 may have a first end 258, a second end 260, and an outer wall 262. The first end 258 of each of the elongate members 252 may be moveable between a gathered position and a dispersed position relative to the longitudinal axis 250 of the drainage manifold 202. When the first end 258 of each of the elongate members 252 is in the gathered position, the elongate members 252 may be releaseably secured longitudinally and circumferentially about the longitudinal axis 250 of the drainage manifold 202. The second end 260 of each of the elongate members 252 may be coupled to the internal surface 136 of the transitional connector 104 and at the first end 130 of the transitional connector 104 such that the drainage tube 106 is in fluid communication with at least the outer wall 262 of each of the elongate members 252. Although FIGS. 2A-2D depict three of the elongate members 252, the drainage manifold 202 may include any number of the elongate members 252 to suit a particular application.

As shown in FIGS. 2A-2D, each of the elongate members 252 may have an oblong cross-sectional shape and may additionally include a longitudinal duct 264, an inner lumen 266, an opening 268, a chamfer 270, a reinforced portion 272, a trimmable tip 274, and a mating surface 276. The longitudinal duct 264 may be positioned on the outer wall 262 and between the first end 258 and the second end 260 of the elongate member 252. As shown in FIGS. 2A-2D, each of the elongate members 252 may include a plurality of longitudinal ducts 264 positioned as described above. The drainage tube 106 may be in fluid communication with at least the longitudinal duct 264 of each of the elongate members 252.

Each of the elongate members 252 may carry the inner lumen 266, for example, internally along the length of the elongate member 252 and between the first and the second end 258, 260 of the elongate member 252. The drainage tube 106 may be in fluid communication with at least the inner lumen 266 in each of the elongate members 252. Each of the elongate members 252 may have the opening 268 disposed through the outer wall 262 of the elongate member 252 to provide fluid communication between the inner lumen 266 of the elongate member 252 and the outer wall 262 of the elongate member 252. The oblong cross-sectional shape of each of the elongate members 252 may enhance the ability of the elongate member 252 to resist collapsing of the inner lumen 266 when positioned at the tissue site 108.

As shown in FIGS. 2A-2D, the opening 268 may be a longitudinal channel 278 positioned between the first and the second end 258, 260 of the elongate member 252. In another embodiment, each of the elongate members 252 may have a plurality of the openings 268 disposed through the outer wall 262 of the elongate member 252. Each of the elongate members 252 may have the chamfer 270 positioned on the abutting surface between the opening 268 and the outer wall 262 of the elongate member 252.

Each of the elongate members 252 may carry the reinforced portion 272 between the first and the second end 258, 260 of the elongate member 252. The reinforced portion 272 may be, for example, a formable titanium wire formed integrally into each of the elongate members 252. Each of the elongate members 252 may carry the trimmable tip 274 at the first end 258 of the elongate member 252. If equipped with the trimmable tip 274, the elongate member 252 may carry the reinforced portion 272 between the trimmable tip 274 and the second end 260 of the elongate member 252. Thus, the trimmable tip 274 may be trimmed or otherwise cut to a desired length without exposing or otherwise interfering with the reinforced portion 272 of the elongate member 252.

Figure 2B:
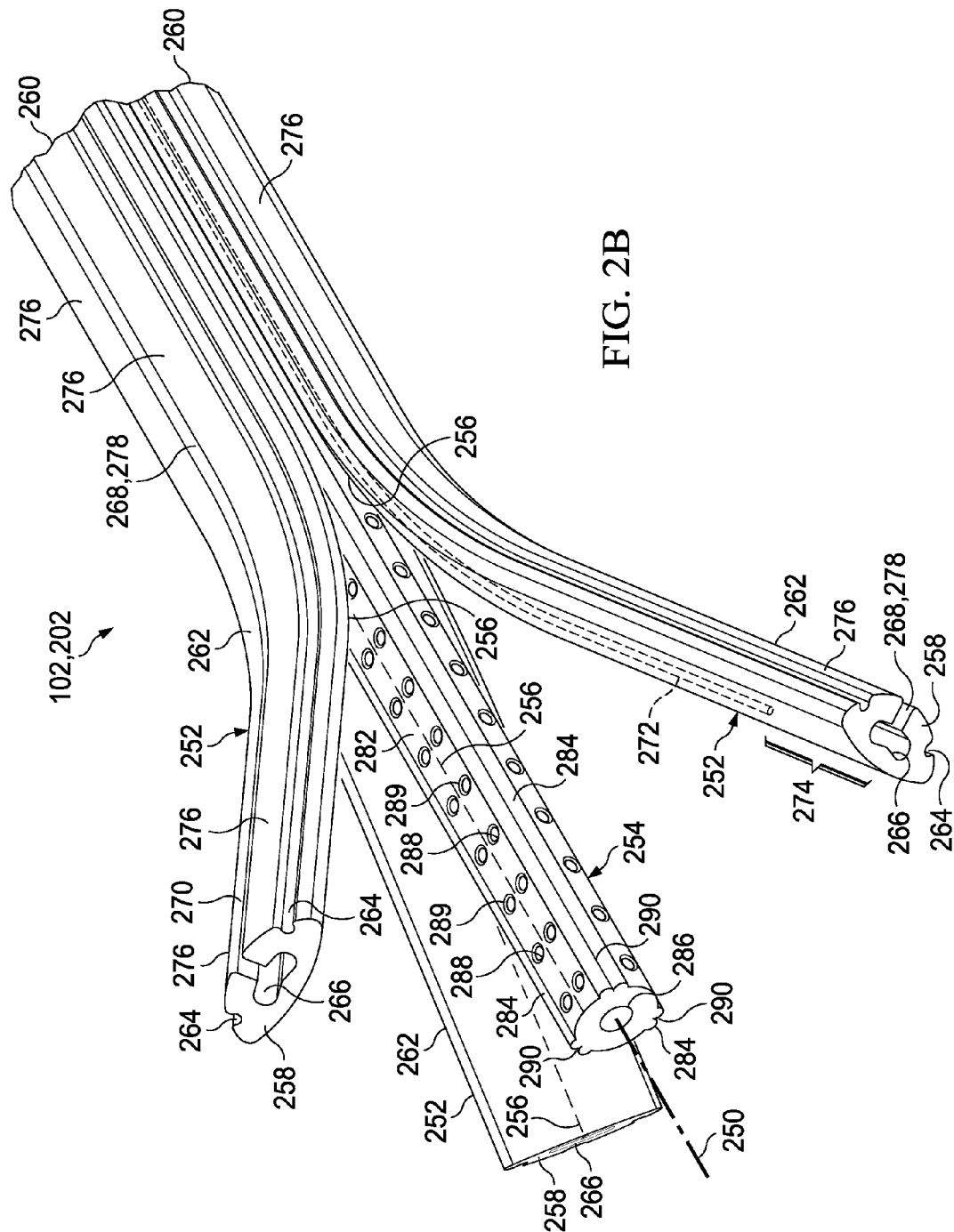
FIG. 2B is a perspective view of the drainage manifold of FIG. 2A, illustrating the plurality of elongate members in a dispersed position.
Figure 2C:
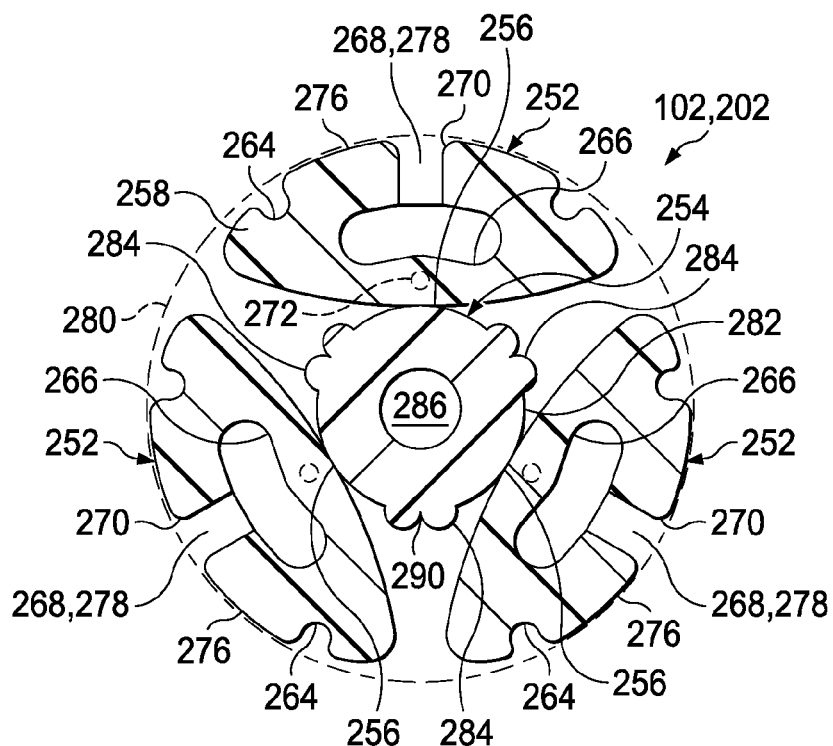
FIG. 2C is a cross-section view of the drainage manifold of FIG. 2A taken at line 2C-2C.
Figure 2D:
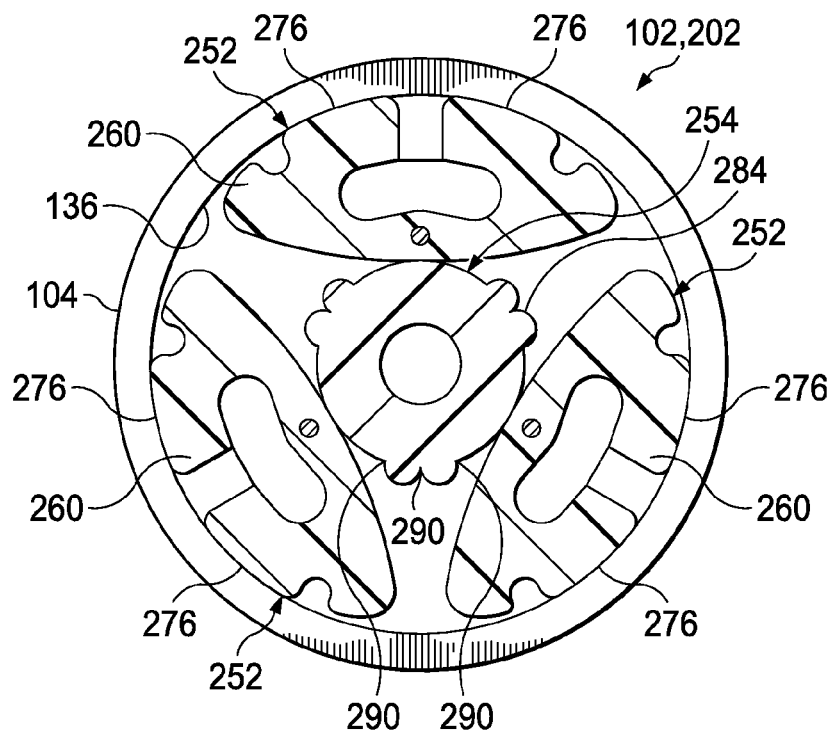
FIG. 2D is a cross-section view of the drainage manifold of FIG. 2A taken at line 2D-2D.

Each of the elongate members 252 may carry the mating surface 276 that may be adapted to engage the internal surface 136 of the transitional connector 104. As shown in FIGS. 2A-2D, the mating surface 276 of each of the elongate members 252 may extend longitudinally between the first and the second end 258, 260 of the elongate member 252 and on the outer wall 262 of the elongate member 252. Further, each of the elongate members 252 may include a plurality of the mating surfaces 276. In another embodiment, each of the elongate members 252 may carry the mating surface 276 on a portion of the elongate member 252 at the second end 260 for engaging the internal surface 136 of the transitional connector 104. The mating surface 276 of each of the elongate members 252 may cooperate with one another to provide an outer boundary 280 for the drainage manifold 202 that may be compatible with the internal surface 136 of the transitional connector 104. For example, as shown in FIGS. 2C-2D, the outer boundary 280 of the drainage manifold 202 may be circular in shape and may have an outer dimension sized to interferingly engage a complementary circular shape and inner dimension of the internal surface 136 of the transitional connector 104.

The elongate support 254 may have a length and an external surface 282. The drainage manifold 202 may carry the elongate support 254 on the longitudinal axis 250 of the drainage manifold 202. When the first end 258 of the elongate member 252 is in the gathered position described above, the elongate member 252 may be releaseably secured longitudinally and circumferentially about the external surface 282 of the elongate support 254. The drainage tube 106 may be in fluid communication with at least the external surface 282 of the elongate support 254.

As shown in FIGS. 2A-2D, the elongate support 254 may additionally include a plurality of longitudinal protrusions 284, an inner lumen 286, an opening 288, and a chamfer 289. The elongate support 254 may carry the plurality of longitudinal protrusions 284 on the external surface 282 and along the length of the elongate support 254. The longitudinal protrusions 284 and the external surface 282 may cooperate to define at least one longitudinal groove 290. The drainage tube 106 may be in fluid communication with at least the longitudinal groove 290.

The elongate support 254 may carry the inner lumen 286, for example, internally along the length of the elongate support 254. The drainage tube 106 may be in fluid communication with at least the inner lumen 286 in the elongate support 254. The elongate support 254 may have the opening 288 disposed through the external surface 282 of the elongate support 254 to provide fluid communication between the inner lumen 286 of the elongate support 254 and the external surface 282 of the elongate support 254. As shown in FIG. 2B, the elongate support 254 may have a plurality of the openings 288 positioned along the length of the elongate support 254. Further, the elongate support 254 may have the chamfer 289 positioned on the abutting surface between the opening 288 and the external surface 282 of the elongate support 254.

The drainage manifold 202 may carry at least one of the sacrificial webs 256 between the elongate member 252 and the elongate support 254 to releaseably secure the elongate member 252 about the elongate support 254 when the first end 258 of the elongate member 252 is in the gathered position. The sacrificial web 256 may be severable upon application of a force, such as a pulling force, directed to pull or otherwise separate the elongate member 252 away from the elongate support 254. For example, the force may be applied on the elongate member 252 and directed transverse to the longitudinal axis 250 of the drainage manifold 202. The thickness of the sacrificial web 256 may be sized such that the sacrificial web 256 may sever upon application of a threshold amount of the force, permitting the elongate member 252 to separate from the elongate support 254. In some embodiments, the threshold amount of the force may be less than an amount of force required to sever another component of the drainage manifold 202. Thus, the application of the threshold force to the elongate member 252 may prevent damage to other components of the drainage manifold 202. In some embodiments, each of the sacrificial webs 256 may, for example, have a score or a perforation (not shown) that may be positioned along the length of the sacrificial web 256 and adapted to enhance the separation of the elongate member 252 from the elongate support 254. For example, the score or perforation may enhance the separation of the elongate member 252 from the elongate support 254 along a predictable or desired path defined by the score or perforation such as, for example, a substantially straight line. The threshold force required to sever the sacrificial web 256 along the score or perforation to separate the elongate member 252 from the elongate support 254 may be less than the force required to sever the sacrificial web 256 at another location. The plurality of the sacrificial webs 256 may permit a physician, for example, to configure the drainage manifold 202 to treat a larger surface area, without a cutting instrument or other instrument, by pulling the elongate members 252 away from the elongate support 254 by hand.

Referring now to the embodiments of FIGS. 3A-3D, a drainage manifold 302 may have a longitudinal axis 350 and may include a plurality of elongate members 352, an elongate support 354, and a plurality of sacrificial webs 356. Each of the elongate members 352 may have a first end 358, a second end 360, and an outer wall 362. The first end 358 of each of the elongate members 352 may be moveable between a gathered position and a dispersed position relative to the longitudinal axis 350 of the drainage manifold 302. When the first end 358 of each of the elongate members 352 is in the gathered position, the elongate members 352 may be releaseably secured longitudinally and circumferentially about the longitudinal axis 350 of the drainage manifold 302. The second end 360 of each of the elongate members 352 may be coupled to the internal surface 136 of the transitional connector 104 at the first end 130 of the transitional connector 104 such that the drainage tube 106 is in fluid communication with at least the outer wall 362 of each of the elongate members 352. Although FIGS. 3A-3D depict four of the elongate members 352, the drainage manifold 302 may include any number of the elongate members 352 to suit a particular application.

As shown in FIGS. 3A-3D, each of the elongate members 352 may additionally include a longitudinal duct 364, a reinforced portion 372, a trimmable tip 374, and a mating surface 376. The longitudinal duct 364 may be positioned on the outer wall 362 and between the first end 358 and the second end 360 of the elongate member 352. As shown in FIGS. 3A-3D, each of the elongate members 352 may include a plurality of longitudinal ducts 364 positioned as described above. The drainage tube 106 may be in fluid communication with at least the longitudinal duct 364 of each of the elongate members 352.

Each of the elongate members 352 may carry the reinforced portion 372 between the first and the second end 358, 360 of the elongate member 352. The reinforced portion 372 may be, for example, a formable titanium wire formed integrally into each of the elongate members 352. Each of the elongate members 352 may carry the trimmable tip 374 at the first end 358 of the elongate member 352. If equipped with the trimmable tip 374, the elongate member 352 may carry the reinforced portion 372 between the trimmable tip 374 and the second end 360 of the elongate member 352. Thus, the trimmable tip 374 may be trimmed or otherwise cut to a desired length without exposing or otherwise interfering with the reinforced portion 372 of the elongate member 352.

Each of the elongate members 352 may carry the mating surface 376 adapted to engage the internal surface 136 of the transitional connector 104. As shown in FIGS. 3A-3D, the mating surface 376 of each of the elongate members 352 may extend longitudinally between the first and the second end 358, 360 of the elongate member 352 and on the outer wall 362 of the elongate member 352. Further, each of the elongate members 352 may include a plurality of the mating surfaces 376. In some embodiments, each of the elongate members 352 may carry the mating surface 376 on a portion of the elongate member 352 at the second end 360 for engaging the internal surface 136 of the transitional connector 104. The mating surface 376 of each of the elongate members 352 may cooperate with one another to provide an outer boundary 380 for the drainage manifold 302 that is compatible with the internal surface 136 of the transitional connector 104. For example, as shown in FIGS. 3C-3D, the outer boundary 380 of the drainage manifold 302 may be circular in shape and may have an outer dimension sized to interferingly engage a complementary circular shape and inner dimension of the internal surface 136 of the transitional connector 104.

The elongate support 354 may have a length and an external surface 382. The drainage manifold 302 may carry the elongate support 354 on the longitudinal axis 350 of the drainage manifold 302. When the first end 358 of the elongate member 352 is in the gathered position described above, the elongate member 352 may be releaseably secured longitudinally and circumferentially about the external surface 382 of the elongate support 354. The drainage tube 106 may be in fluid communication with at least the external surface 382 of the elongate support 354.

Figure 3A:
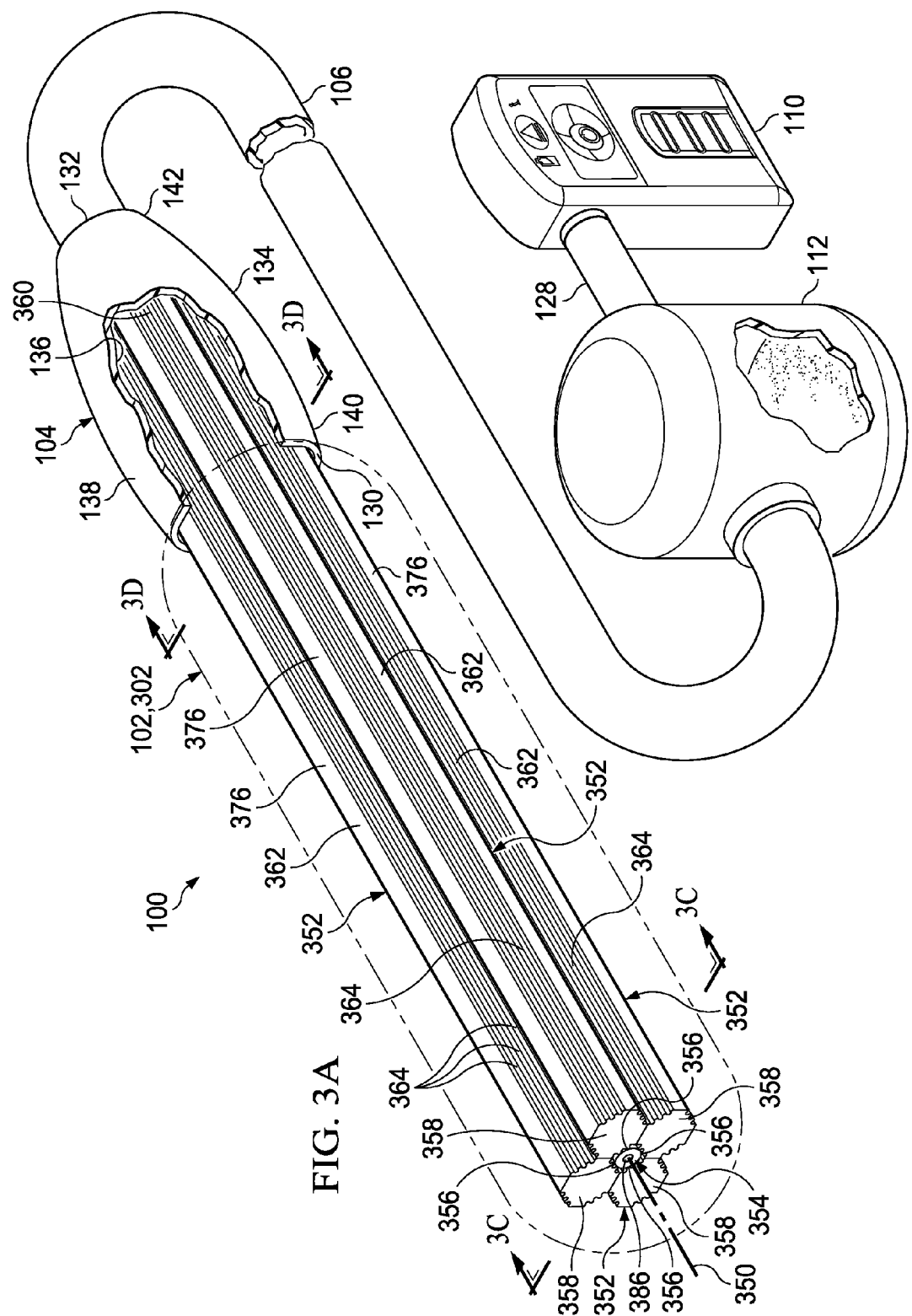
FIG. 3A is a perspective, cut-away view of another illustrative embodiment of a drainage system depicting a drainage manifold having a plurality of elongate members in a gathered position.
Figure 3B:
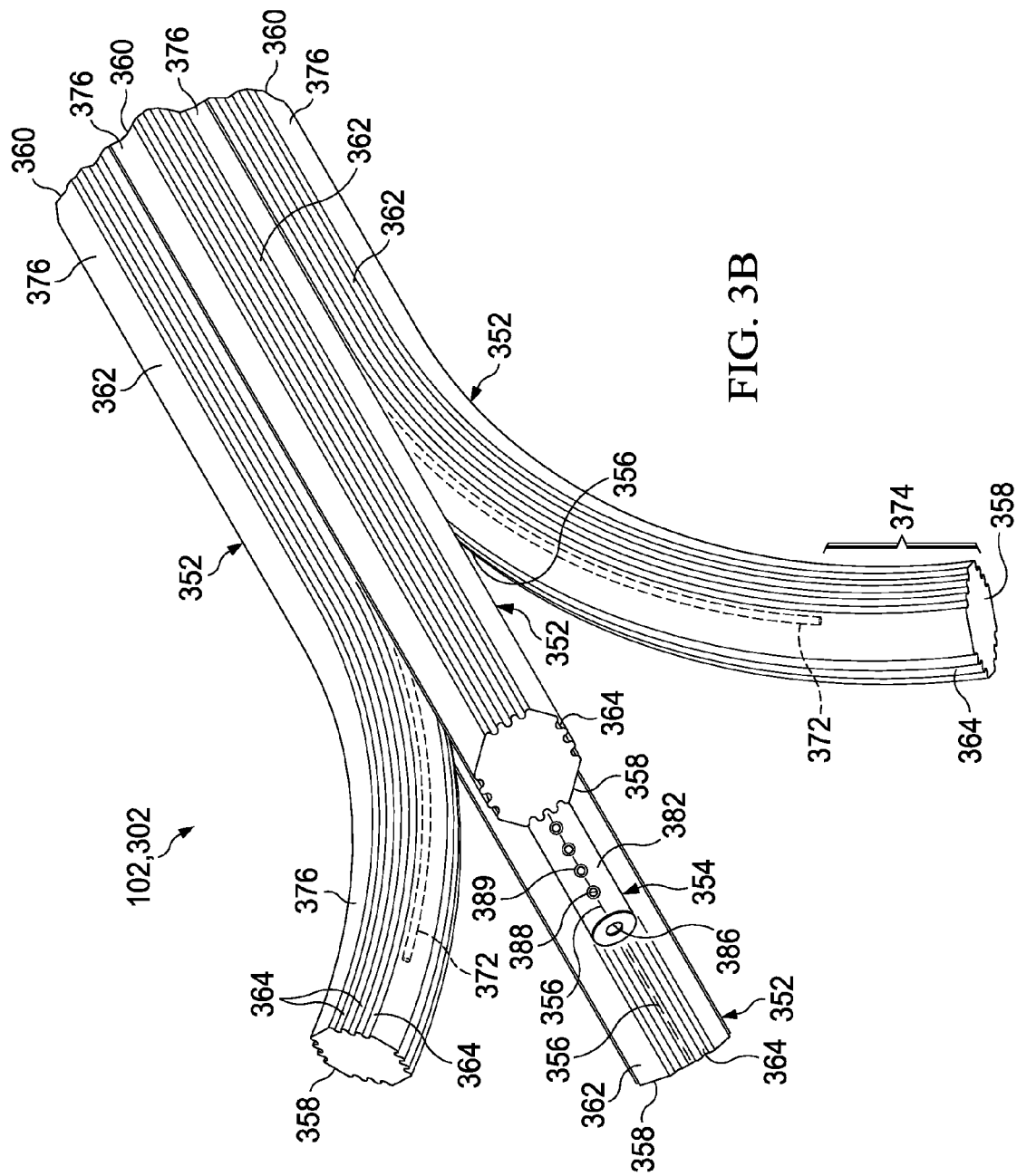
FIG. 3B is a perspective view of the drainage manifold of FIG. 3A, illustrating the plurality of elongate members in a dispersed position.
Figure 3C:
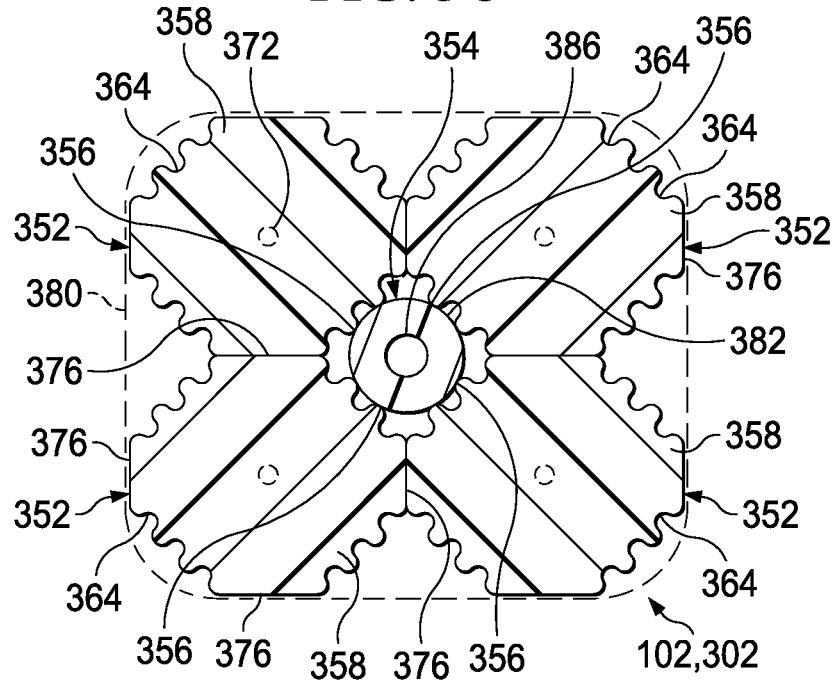
FIG. 3C is a cross-section view of the drainage manifold of FIG. 3A taken at line 3C-3C.
Figure 3D:
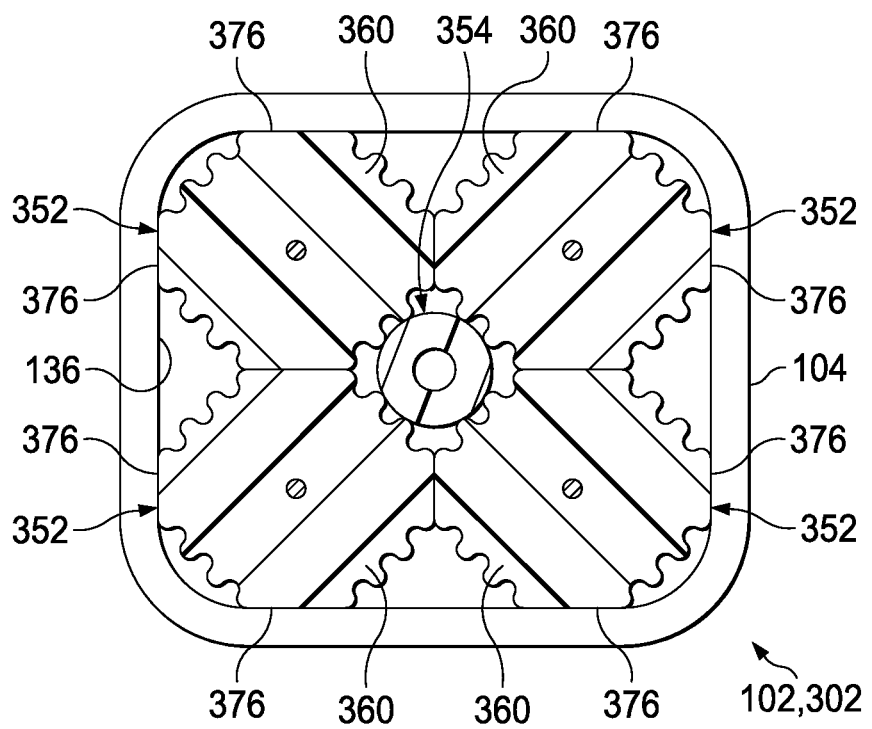
FIG. 3D is a cross-section view of the drainage manifold of FIG. 3A taken at line 3D-3D.

As shown in FIGS. 3A-3D, the elongate support 354 may additionally include an inner lumen 386, an opening 388, and a chamfer 389. The elongate support 354 may carry the inner lumen 386, for example, internally along the length of the elongate support 354. The drainage tube 106 may be in fluid communication with at least the inner lumen 386 in the elongate support 354. The elongate support 354 may have the opening 388 disposed through the external surface 382 of the elongate support 354 to provide fluid communication between the inner lumen 386 of the elongate support 354 and the external surface 382 of the elongate support 354. As shown in FIG. 3B, the elongate support 354 may have a plurality of the openings 388 positioned along the length of the elongate support 354. Further, the elongate support 354 may have the chamfer 389 positioned on the abutting surface between the opening 388 and the external surface 382 of the elongate support 354.

In some embodiments (not shown) the elongate support 354 may have similar elements as the elongate member 352. For example, the elongate support 354 may include the previously described longitudinal duct 364, the reinforced portion 372, and the trimmable tip 374. The elongate support 354 may carry the longitudinal duct 364 along the length and on the external surface 382 of the elongate support 354. Further, the elongate support 354 may carry the trimmable tip 374 on an end of the elongate support 354 with the reinforced portion 372 positioned between the trimmable tip 374 and an opposing end of the elongate support 354.

The drainage manifold 302 may carry at least one of the sacrificial webs 356 between the elongate member 352 and the elongate support 354 to releaseably secure the elongate member 352 about the elongate support 354 when the first end 358 of the elongate member 352 is in the gathered position. The sacrificial web 356 may be severable upon application of a force, such as a pulling force, directed to pull or otherwise separate the elongate member 352 away from the elongate support 354. For example, the force may be applied on the elongate member 352 and directed transverse to the longitudinal axis 350 of the drainage manifold 302. The thickness of the sacrificial web 356 may be sized such that the sacrificial web 356 may sever upon application of a threshold amount of the force, permitting the elongate member 352 to separate from the elongate support 354. In some embodiments, the threshold amount of the force may be less than an amount of force capable of severing another component of the drainage manifold 302. Thus, the application of the threshold force to the elongate member 352 may prevent damage to other components of the drainage manifold 302. In some embodiments, each of the sacrificial webs 356 may, for example, have a score or a perforation (not shown) along the length of the sacrificial web 356 that may be adapted to enhance the separation of the elongate member 352 from the elongate support 354. For example, the score or perforation may define a predictable or desired path, such as a substantially straight line, for separation of the elongate member 352 from the elongate support 354.

The threshold force required to sever the sacrificial web 356 along the score or perforation to separate the elongate member 352 from the elongate support 354 may be less than the force required to sever the sacrificial web 356 at another location. The plurality of the sacrificial webs 356 may permit a physician, for example, to configure the drainage manifold 302 to treat a larger surface area of tissue, without a cutting instrument or other instrument, by pulling the elongate members 352 away from the elongate support 354 by hand.

Referring now to the embodiments of FIGS. 4A-4D, a drainage manifold 402 may have a longitudinal axis 450 and may include a plurality of elongate members 452 and a plurality of sacrificial webs 456. Each of the elongate members 452 may have a first end 458, a second end 460, and an outer wall 462. The first end 458 of each of the elongate members 452 may be moveable between a gathered position and a dispersed position relative to the longitudinal axis 450 of the drainage manifold 402. When the first end 458 of each of the elongate members 452 is in the gathered position, the elongate members 452 may be releaseably secured longitudinally and circumferentially about the longitudinal axis 450 of the drainage manifold 402. The second end 460 of each of the elongate members 452 may be coupled to the internal surface 136 of the transitional connector 104 at the first end 130 of the transitional connector 104 such that the drainage tube 106 may be in fluid communication with at least the outer wall 462 of each of the elongate members 452. Although FIGS. 4A-4D depict three of the elongate members 452, the drainage manifold 402 may include any number of the elongate members 452 to suit a particular application.

As shown in FIGS. 4A-4D, each of the elongate members 452 may have an oblong cross-sectional shape and may additionally include a longitudinal duct 464, an inner lumen 466, an opening 468, a chamfer 470, a reinforced portion 472, a trimmable tip 474, and a mating surface 476. The longitudinal duct 464 may be positioned on the outer wall 462 and between the first end 458 and the second end 460 of the elongate member 452. In some embodiments, each of the elongate members 452 may include a plurality of the longitudinal ducts 464 positioned as described above. The drainage tube 106 may be in fluid communication with at least the longitudinal duct 464 of each of the elongate members 452.

Each of the elongate members 452 may carry the inner lumen 466, for example, internally along the length of the elongate member 452 and between the first and the second end 458, 460 of the elongate member 452. The drainage tube 106 may be in fluid communication with at least the inner lumen 466 in each of the elongate members 452. Each of the elongate members 452 may have the opening 468 disposed through the outer wall 462 of the elongate member 452 to provide fluid communication between the inner lumen 466 of the elongate member 452 and the outer wall 462 of the elongate member 452. The oblong cross-sectional shape of each of the elongate members 452 may enhance the ability of the elongate member 452 to resist collapsing of the inner lumen 466 when positioned at the tissue site 108.

As shown in FIGS. 4A-4D, each of the elongate members 452 may have a plurality of the openings 468 disposed through the outer wall 462 of the elongate member 452. The plurality of the openings 468 may be positioned sequentially between the first and the second end 458, 460 of each of the elongate members 452. Each of the elongate members 452 may have the chamfer 470 positioned on the abutting surface between the opening 468 and the outer wall 462 of the elongate member 452.

Each of the elongate members 452 may carry the reinforced portion 472 between the first and the second end 458, 460 of the elongate member 452. The reinforced portion 472 may be, for example, a formable titanium wire formed integrally into each of the elongate members 452. Each of the elongate members 452 may carry the trimmable tip 474 at the first end 458 of the elongate member 452. If equipped with the trimmable tip 474, the elongate member 452 may carry the reinforced portion 472 between the trimmable tip 474 and the second end 460 of the elongate member 452. Thus, the trimmable tip 474 may be trimmed or otherwise cut to a desired length without exposing or otherwise interfering with the reinforced portion 472 of the elongate member 452.

Figure 4B:
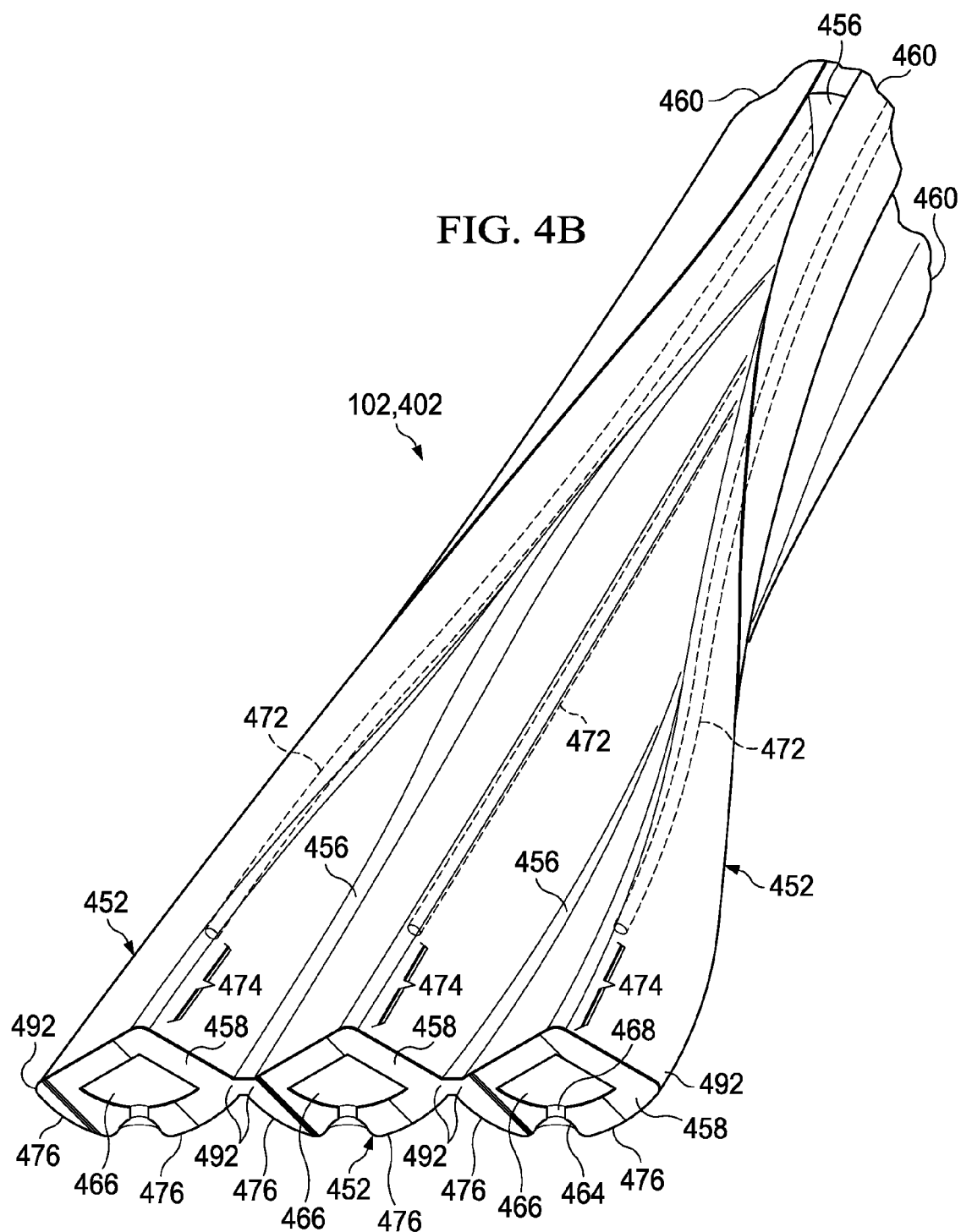
FIG. 4B is a perspective view of the drainage manifold of FIG. 4A, illustrating the plurality of elongate members in a dispersed position.
Figure 4C:
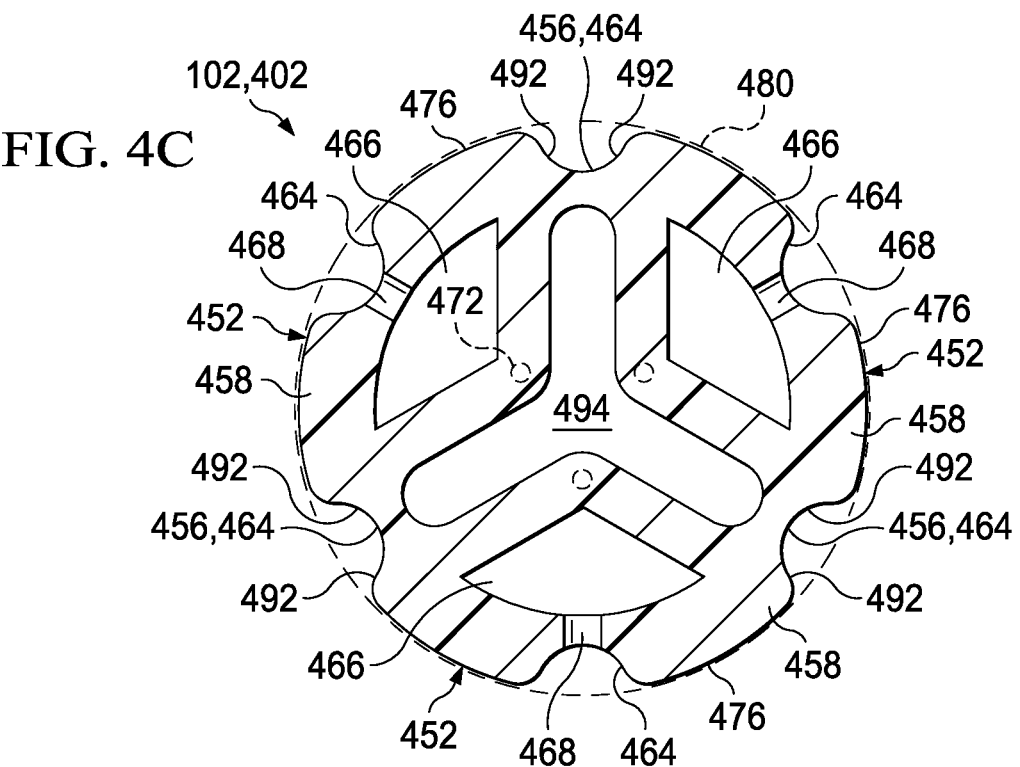
FIG. 4C is a cross-section view of the drainage manifold of FIG. 4A taken at line 4C-4C.
Figure 4D:
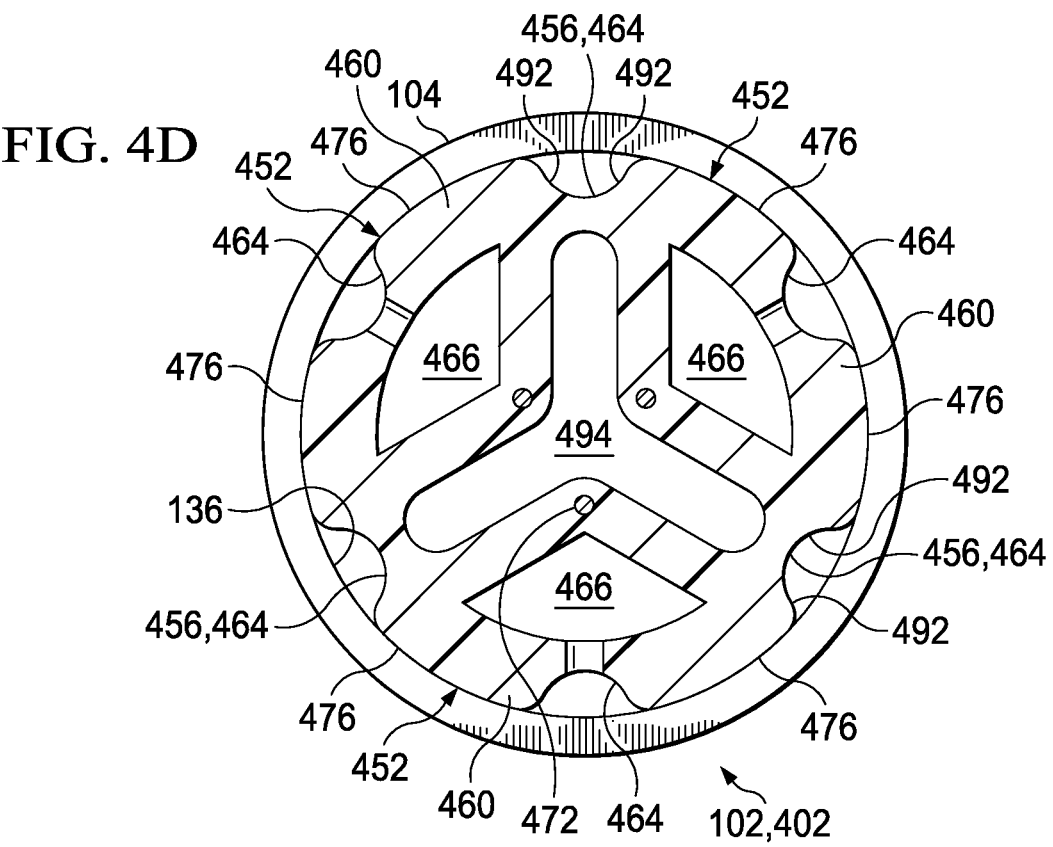
FIG. 4D is a cross-section view of the drainage manifold of FIG. 4A taken at line 4D-4D.

Each of the elongate members 452 may carry the mating surface 476 that may be adapted to engage the internal surface 136 of the transitional connector 104. As shown in FIGS. 4A-4D, the mating surface 476 of each of the elongate members 452 may extend longitudinally between the first and the second end 458, 460 of the elongate member 452 and on the outer wall 462 of the elongate member 452. Further, each of the elongate members 452 may include a plurality of the mating surfaces 476. In some embodiments, each of the elongate members 452 may carry the mating surface 476 on a portion of the elongate member 452 at the second end 460 for engaging the internal surface 136 of the transitional connector 104. The mating surface 476 of each of the elongate members 452 may cooperate with one another to provide an outer boundary 480 for the drainage manifold 402 that is compatible with the internal surface 136 of the transitional connector 104. For example, as shown in FIGS. 4C-4D, the outer boundary 480 of the drainage manifold 402 may be circular in shape and may have an outer dimension sized to interferingly engage a complementary circular shape and inner dimension of the internal surface 136 of the transitional connector 104.

The drainage manifold 402 may carry the sacrificial webs 456 circumferentially about the longitudinal axis 450 of the drainage manifold 402 and between the elongate members 452 to releaseably secure the elongate members 452 to one another when the first end 458 of each of the elongate members 452 is in the gathered position. For example, as shown in FIGS. 4A-4D, each of the elongate members 452 may have an oblong cross-sectional shape having a width dimension greater than a height dimension. Each of the elongate members 452 may have a pair of opposing sides 492 separated by the width of the elongate member 452. When the first end 458 of each of the elongate members 452 is in the gathered position, each of the sides 492 of one of the elongate members 452 may be adjacent one of the sides 492 of another elongate member 452. The drainage manifold 402 may carry at least one of the sacrificial webs 456 between the adjacent sides 492 of the elongate members 452.

Each of the sacrificial webs 456 may be severable upon application of a force, such as a pulling force, directed to pull or otherwise separate one of the elongate members 452 away from another of the elongate members 452. For example, the force may be applied on one of the elongate members 452 and directed transverse to the longitudinal axis 450 of the drainage manifold 402. The thickness of the sacrificial web 456 may be sized such that the sacrificial web 456 may sever upon application of a threshold amount of the force, permitting the elongate member 452 to separate from the other elongate members 452. In some embodiments, the threshold amount of the force may be less than an amount of force required to sever other components of the drainage manifold 402. Thus, the application of the threshold force to the elongate member 452 may prevent damage to other components of the drainage manifold 402. In some embodiments, each of the sacrificial webs 456 may, for example, have a score or a perforation (not shown) along the length of the sacrificial web 456 that may be adapted to enhance the separation of the elongate members 452 from one another. For example, the score or perforation may define a predictable or desired path, such as a substantially straight line, for the separation of the elongate members 452 from one another. The threshold force required to sever the sacrificial web 456 along the score or perforation to separate the elongate members 452 from one another may be less than the force required to sever the sacrificial web 456 at another location. The plurality of the sacrificial webs 456 may permit a physician, for example, to configure the drainage manifold 402 to treat a larger surface area, without a cutting instrument or other instrument, by pulling the elongate members 452 away from one another and away from the longitudinal axis 450 of the drainage manifold 402.

As shown in FIGS. 4A-4D, the outer wall 462 of each of the elongate members 452 may cooperate with one another and with each of the sacrificial webs 456 to define a central lumen 494 in the drainage manifold 402 when the first end 458 of each of the elongate members 452 is in the gathered position. The drainage tube 106 may be in fluid communication with at least the central lumen 494 in the drainage manifold 402. Further, as shown, at least one of the sacrificial webs 456 may coincide with at least one of the longitudinal ducts 464.

Figure 5A:
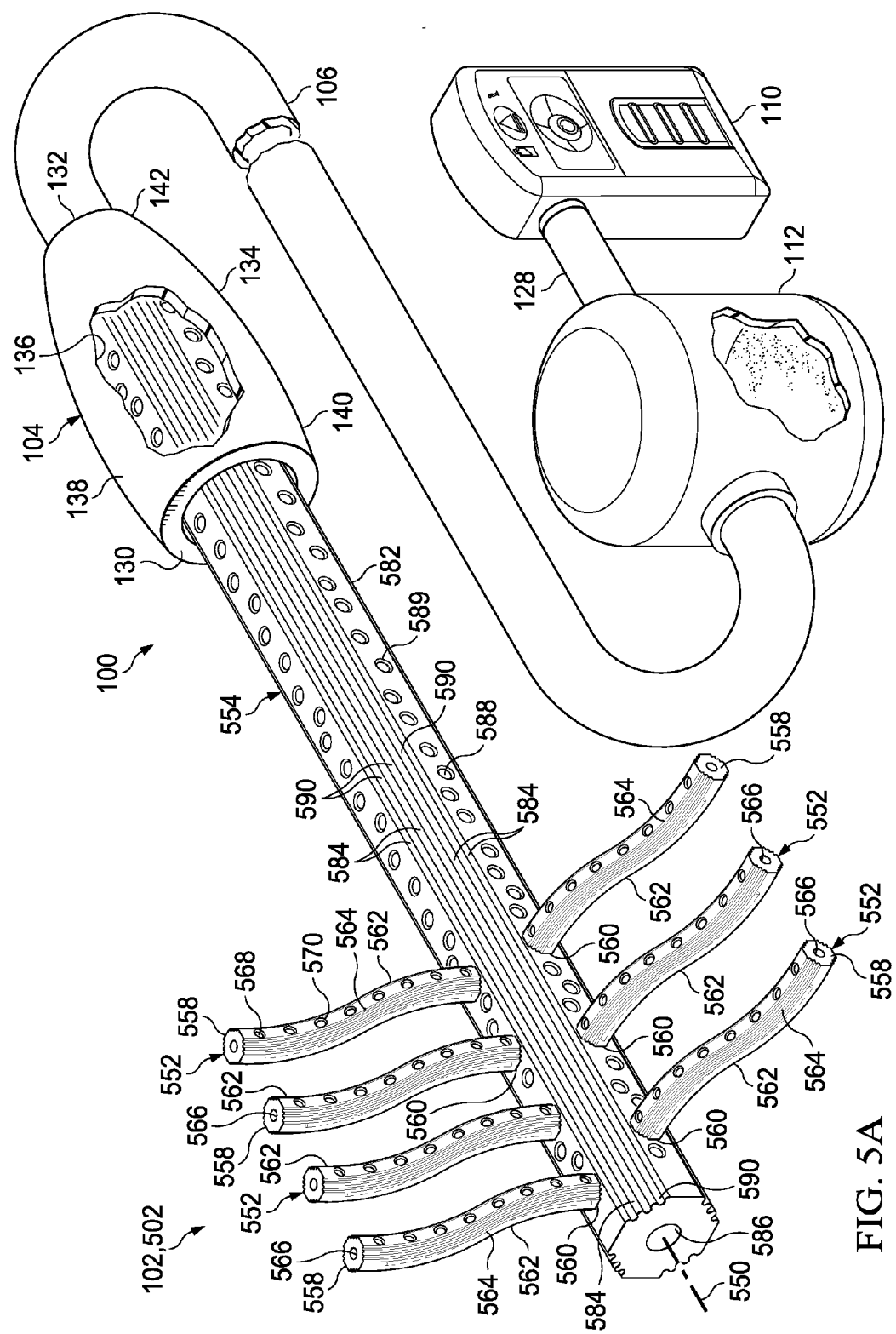
FIG. 5A is a perspective, cut-away view of another illustrative embodiment of a drainage system depicting a drainage manifold having a plurality of elongate members.
Figure 5B:
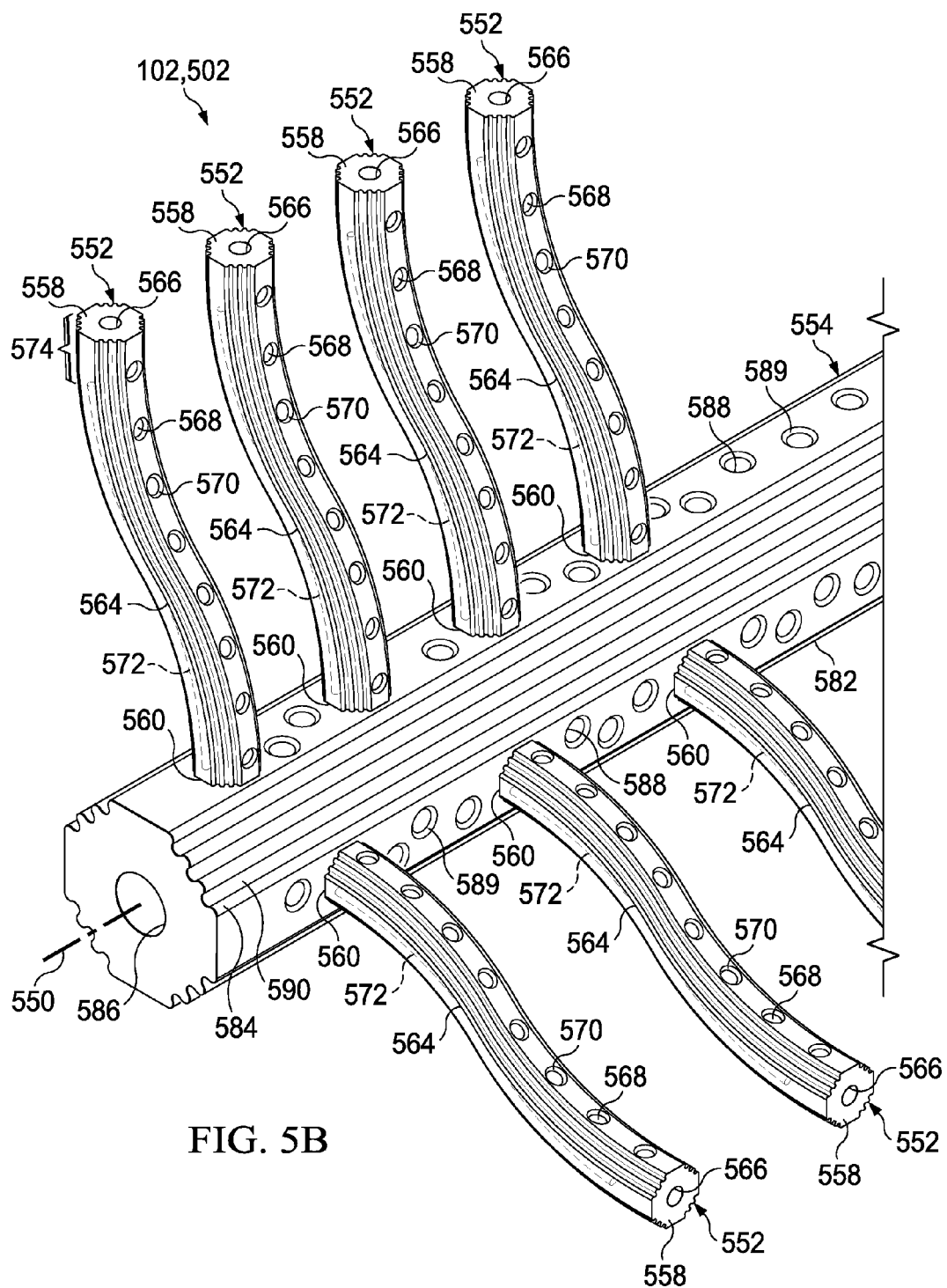
FIG. 5B is a perspective view of the drainage manifold depicted in FIG. 5A.

Referring now to the embodiments of FIGS. 5A-5B, the drainage manifold 502 may have a longitudinal axis 550 and may include a plurality of elongate members 552 and an elongate support 554. The elongate support 554 may have a length and an external surface 582 positioned on the longitudinal axis 550 of the drainage manifold 502. Each of the elongate members 552 may have a first end 558, a second end 560, and an outer wall 562. The first end 558 of each of the elongate members 552 may be moveable relative to the elongate support 554. The second end 560 of each of the elongate members 552 may be secured about the external surface 582 of the elongate support 554. The elongate support 554 may be coupled to the internal surface 136 of the transitional connector 104 at the first end 130 of the transitional connector 104 such that the drainage tube 106 may be in fluid communication with at least the outer wall 562 of each of the elongate members 552 and the external surface 582 of the elongate support 554.

The drainage manifold 502 may include any number of the elongate members 552 to suit a particular application. Further, the elongate members 552 may form an angle (not shown) relative to the elongate support 554, such as, for example, an angle of about 45 degrees measured between the elongate member 552 and the elongate support 554. The angle may reduce the trauma experienced by the patient upon withdrawal of the drainage manifold 502.

As shown in FIGS. 5A-5B, each of the elongate members 552 may additionally include a longitudinal duct 564, an inner lumen 566, an opening 568, a chamfer 570, a reinforced portion 572, and a trimmable tip 574. The longitudinal duct 564 may be positioned on the outer wall 562 and between the first end 558 and the second end 560 of the elongate member 552. As shown in FIGS. 5A-5B, each of the elongate members 552 may include a plurality of the longitudinal ducts 564 positioned as described above. The drainage tube 106 may be in fluid communication with at least the longitudinal duct 564 of each of the elongate members 552.

Each of the elongate members 552 may carry the inner lumen 566, for example, internally along the length of the elongate member 552 and between the first and the second end 558, 560 of the elongate member 552. The drainage tube 106 may be in fluid communication with at least the inner lumen 566 in each of the elongate members 552. Each of the elongate members 552 may have the opening 568 disposed through the outer wall 562 of the elongate member 552 to provide fluid communication between the inner lumen 566 of the elongate member 552 and the outer wall 562 of the elongate member 552. In some embodiments, each of the elongate members 552 may have a plurality of the openings 568 disposed through the outer wall 562 of the elongate member 552. Each of the elongate members 552 may have the chamfer 570 positioned on the abutting surface between the opening 568 and the outer wall 562 of the elongate member 552.

Each of the elongate members 552 may carry the reinforced portion 572 between the first and the second end 558, 560 of the elongate member 552. The reinforced portion 572 may be, for example, a formable titanium wire formed integrally into each of the elongate members 552. Each of the elongate members 552 may carry the trimmable tip 574 at the first end 558 of the elongate member 552. If equipped with the trimmable tip 574, the elongate member 552 may carry the reinforced portion 572 between the trimmable tip 574 and the second end 560 of the elongate member 552. Thus, the trimmable tip 574 may be trimmed or otherwise cut to a desired length without exposing or otherwise interfering with the reinforced portion 572 of the elongate member 552.

As shown in FIGS. 5A-5B, the elongate support 554 may additionally include a plurality of longitudinal protrusions 584, an inner lumen 586, an opening 588, and a chamfer 589. The elongate support 554 may carry the plurality of longitudinal protrusions 584 on the external surface 582 and along the length of the elongate support 554. The longitudinal protrusions 584 and the external surface 582 cooperate to define at least one longitudinal groove 590. The drainage tube 106 may be in fluid communication with at least the longitudinal groove 590.

The elongate support 554 may carry the inner lumen 586, for example, internally along the length of the elongate support 554. The drainage tube 106 may be in fluid communication with at least the inner lumen 586 in the elongate support 554 and the outer wall 562 of each of the elongate members 552. The elongate support 554 may have the opening 588 disposed through the external surface 582 of the elongate support 554 to provide fluid communication between the inner lumen 586 of the elongate support 554 and the external surface 582 of the elongate support 554. As shown in FIGS. 5A-5B, the elongate support 554 may have a plurality of the openings 588 positioned along the length of the elongate support 554. Further, the elongate support 554 may have the chamfer 589 positioned on the abutting surface between the opening 588 and the external surface 582 of the elongate support 554.

Referring generally to the drawings, in some embodiments, insertion of the drainage tube 106 through the incision 120 occurs with the drainage tube 106 beginning at the tissue site 108 and proceeding through the subcutaneous tissue 126, the dermis 124, and subsequently protruding through the epidermis 122. The drainage tube 106 may be draped with an external sealing member (not shown) in any suitable manner to enhance the seal of the drainage tube about the epidermis 122, external to the incision 120. The sealing member may be, for example, an adhesive polyurethane sheet or any material capable of providing a fluid seal suitable to maintain reduced pressure at the tissue site 108. As shown in FIG. 1, the transitional connector 104 may reside between the incision 120 and the tissue site 108, thereby permitting the incision 120 to seal about the drainage tube 106 at the epidermis 122 without requiring the external sealing member described above. In some embodiments, the transitional connector 104 may reside exterior to the incision 120 and the epidermis 122.

Through the single incision 120, the drainage manifold 102, 202, 302, 402, 502 may be configured to treat a large surface area at the tissue site 108 by hand and without the need for an instrument or tool. Specifically, the elongate members 252, 352, 452 may be separated as described above and positioned, for example, in the cavities 116 and between the tissue layers 118 in and around the tissue site 108. Similarly, the elongate members 552 may be moved about the elongate support 554 and positioned in and around the tissue site 108 in a similar manner as described above.

The reinforced portion 272, 372, 472, 572 may enhance the ability of the elongate members 252, 352, 452, 552 to retain a desired shape when positioned at the tissue site 108. Forming the reinforced portion 272, 372, 472, 572 into a desired shape may enhance the ability of a physician, for example, to configure the drainage manifold 102, 202, 302, 402, 502 to remain in fluid communication with the cavities 116 and the tissue layers 118 that may be present at the tissue site 108. For example, the tissue site 108 may have a unique size and shape requiring the drainage manifold 102, 202, 302, 402, 502 to be configured and positioned in a particular manner to reduce the possibility for fluids to become trapped at the tissue site 108. Fluids may become trapped at the tissue site 108, for example, in the cavities 116 and between the tissue layers 118 if the drainage manifold 102, 202, 302, 402, 502 does not remain in fluid communication with the cavities 116 and the tissue layers 118. Fluids trapped at the tissue site 108 may increase the chance for seroma or hematoma to occur. To enhance the ability of the elongate members 252, 352, 452, 552 to retain a desired shape and position at the tissue site 108, the physician may optionally utilize, for example, a biodegradable suture material and/or two-dimensional mesh material to secure the elongate members 252, 352, 452, 552 in and around the tissue site 108.

The trimmable tip 274, 374, 474, 574 may provide a portion of each of the respective elongate members 252, 352, 452, 552 suitable for trimming to a desired size to fit in and around the tissue site 108. Trimming the trimmable tip 274, 374, 474, 574 may not interfere with the reinforced portion 272, 372, 472, 572 or the operation of the drainage manifold 102, 202, 302, 402, 502.

As described above, the reduced-pressure source 110 may be in fluid communication with the drainage manifold 102, 202, 302, 402, 502. The drainage manifold 102, 202, 302, 402, 502 may be positioned at the tissue site 108 as described above and may be adapted to distribute reduced pressure from the reduced-pressure source 110 to the tissue site 108. Providing reduced pressure from the reduced-pressure source 110 to the drainage manifold 102, 202, 302, 402, 502 and the tissue site 108 may extract fluid from the tissue site 108. Further, distributing the reduced pressure to the tissue site 108 may exert force on the tissue site 108 that, for example, may draw the cavities 116 and the tissue layers 118 together and around the components of the drainage manifold 102, 202, 302, 402, 502. When reduced pressure is applied, the drainage tube 106 may remain in fluid communication with the components of the drainage manifold 102, 202, 302, 402, 502 as previously described. The components of the drainage manifold 102, 202, 302, 402, 502 may provide a separation or a fluid passageway between the drainage manifold 102, 202, 302, 402, 502 and, for example, the tissue layers 118. Thus, the previously described components of the drainage manifold 102, 202, 302, 402, 502 positioned at the tissue site 108 may cooperate with the tissue site 108 to form a network of fluid passageways with the tissue site 108 when the reduced pressure is applied. Fluid extracted from the tissue site 108 may travel in and along the fluid passageways and the previously described components of the drainage manifold 102, 202, 302, 402, 502 to the transitional connector 104 and through the drainage tube 106. The fluid may exit the drainage tube 106 into the fluid canister 112 for storage and disposal.

At the conclusion of treatment, the drainage manifold 102, 202, 302, 402, 502 may be withdrawn from the tissue site 108 by applying traction or otherwise pulling on the drainage tube 106, thereby withdrawing the transitional connector 104 and the drainage manifold 102, 202, 302, 402, 502 through the incision 120. Upon withdrawal, the drainage manifold 202, 302, 402 may retain a shape substantially similar to the shape of the drainage manifold 202, 302, 402 prior to placement at the tissue site 108. For example, the previously described components of the drainage manifold 202, 302, 402 may, upon withdrawal, retain the previously described configuration about the respective longitudinal axis 250, 350, 450 of the drainage manifold 202, 302, 402. In this manner, the drainage manifold 202, 302, 402 may reduce pain experienced by the patient during withdrawal.

Although this specification discloses the drainage system 100 in the context of certain illustrative, non-limiting embodiments, various changes, substitutions, permutations, and alterations may be made without departing from the scope of the specification as defined by the appended claims. Further, any feature described in connection with any one embodiment may also be applicable to any other embodiment.

What is claimed is:

1. A drainage system for draining fluid from a tissue site, comprising:
  a drainage manifold having a longitudinal axis, and comprising:
    an elongate support having a length and an external surface, the length of the elongate support positioned on the longitudinal axis of the drainage manifold;
    a plurality of elongate members each having a first end, a second end, and an outer wall, the first end of each of the elongate members moveable between a gathered position and a dispersed position relative to the longitudinal axis of the drainage manifold, wherein when the first end of each of the elongate members is in the gathered position, each elongate member is releasably secured longitudinally and circumferentially about the external surface of the elongate support, and wherein each of the elongate members has an oblong cross-sectional shape, each of the elongate members comprising:
      at least one opening disposed through the outer wall of the elongate member to provide fluid communication between an inner lumen of the elongate member and the outer wall of the elongate member;

a longitudinal duct positioned on the outer wall and between the first end and the second end; and
a reinforced portion positioned between the first end and the second end;
a transitional connector having a first end and an opposing second end, the first end coupled to the drainage manifold; and
a drainage tube coupled to the second end of the transitional connector and in fluid communication with the drainage manifold and the longitudinal duct of each of the elongate members.

2. The drainage system of claim 1, further comprising a reduced-pressure source fluidly coupled to the drainage tube and adapted to provide a reduced pressure to the drainage manifold.

3. The drainage system of claim 2, further comprising a fluid canister positioned in fluid communication between the drainage tube and the reduced-pressure source, wherein the fluid canister is adapted to retain fluid communicated from the drainage manifold.

4. The drainage system of claim 1, wherein the elongate support has an inner lumen, and wherein the drainage tube is in fluid communication with the inner lumen of the elongate support.

5. The drainage system of claim 4, wherein the elongate support has an opening disposed through the external surface of the elongate support to provide fluid communication between the inner lumen of the elongate support and the external surface of the elongate support.

6. The drainage system of claim 1, wherein the external surface of the elongate support has a plurality of longitudinal protrusions positioned along the length of the elongate support, the longitudinal protrusions and the external surface cooperating to define a longitudinal groove, wherein the drainage tube is in fluid communication with the longitudinal groove.

7. The drainage system of claim 1, the drainage manifold further comprising a plurality of sacrificial webs, at least one of the sacrificial webs positioned between the elongate member and the elongate support to releasably secure the elongate member about the elongate support when the first end of the elongate member is in the gathered position.

8. The drainage system of claim 1, wherein each of the elongate members further comprise a chamfer positioned on an abutting surface between the at least one opening and the outer wall of the elongate member.

9. The drainage system of claim 1, wherein the at least one opening is a longitudinal channel positioned between the first end and the second end of the elongate member.

10. The drainage system of claim 1, the drainage manifold further comprising a plurality of sacrificial webs positioned circumferentially about the longitudinal axis of the drainage manifold and releasingly secured between the elongate members when the first end of each of the elongate members is in the gathered position.

11. The drainage system of claim 10, wherein the outer wall of each of the elongate members cooperate with one another and with each of the sacrificial webs to define a central lumen in the drainage manifold when the first end of each of the elongate members is in the gathered position, and wherein the drainage tube is in fluid communication with the central lumen.

12. The drainage system of claim 1, wherein each of the elongate members further comprise a plurality of openings disposed through the outer wall of the elongate member to provide fluid communication between the inner lumen of the elongate member and the outer wall of the elongate member, the plurality of openings positioned sequentially between the first end and the second end of the elongate member.

13. The drainage system of claim 1, wherein each of the elongate members further comprise a trimmable tip positioned at the first end of the elongate member, and wherein the reinforced portion of the elongate member extends from the trimmable tip to the second end of the elongate member.

14. The drainage system of claim 1, wherein the second end of each of the elongate members are coupled to an internal surface of the transitional connector at the first end of the transitional connector.

15. The drainage system of claim 14, wherein each of the elongate members further comprise a mating surface positioned on the outer wall of the elongate member and adapted to engage the internal surface of the transitional connector.

16. The drainage system of claim 15, wherein the mating surface of each of the elongate members cooperate with one another to provide an outer boundary for the drainage manifold that is compatible with the internal surface of the transitional connector.

17. The drainage system of claim 15, wherein the mating surface of each of the elongate members extends longitudinally between the first end and the second end of the elongate member.

18. The drainage system of claim 14, wherein the internal surface of the transitional connector has a substantially circular cross-section.

19. A drainage manifold for draining fluid from a tissue site, the drainage manifold comprising:
a longitudinal axis;
an elongate support having a length, an external surface, and an inner lumen, the length of the elongate support positioned on the longitudinal axis of the drainage manifold;
a plurality of elongate members each having a first end, a second end, and an outer wall, the first end of each of the elongate members moveable between a gathered position and a dispersed position relative to the longitudinal axis of the drainage manifold, wherein when the first end of the elongate member is in the gathered position, each elongate member is releasably secured longitudinally and circumferentially about the external surface of the elongate support, and wherein each of the elongate members has an oblong cross-sectional shape, each of the elongate members comprising:
a longitudinal duct positioned on the outer wall and between the first end and the second end;
an inner lumen; and
an opening disposed through the outer wall, the opening providing fluid communication between the inner lumen of the elongate member and the outer wall of the elongate member;
a plurality of sacrificial webs, at least one of the sacrificial webs positioned between the elongate member and the elongate support to releasably secure the elongate member about the elongate support when the first end of the elongate member is in the gathered position.

20. The drainage manifold of claim 19, each of the elongate members further comprising a reinforced portion positioned between the first end and the second end of the elongate member.

21. The drainage manifold of claim 19, wherein the elongate support has an opening disposed through the external surface of the elongate support to provide fluid communication between the inner lumen of the elongate support and the external surface of the elongate support.

22. The drainage manifold of claim 19, wherein the external surface of the elongate support has a plurality of longitudinal protrusions positioned along the length of the elongate support, the longitudinal protrusions and the external surface cooperating to define a longitudinal groove.

23. The drainage manifold of claim 19, wherein the opening disposed through the outer wall of the elongate member is a longitudinal channel positioned between the first end and the second end of the elongate member.

24. The drainage manifold of claim 19, wherein each of the elongate members further comprise a mating surface positioned on the outer wall of the elongate member and extending longitudinally between the first end and the second end of the elongate member, wherein the mating surface of each of the elongate members cooperate with one another to define an outer boundary of the drainage manifold.

25. The drainage manifold of claim 24, wherein the outer boundary of the drainage manifold is circular in shape.

26. The drainage manifold of claim 19, wherein the elongate support comprises a longitudinal duct positioned along the length and on the external surface of the elongate support.

* * * * *